United States Patent [19]

Manero et al.

[11] Patent Number: 5,512,207
[45] Date of Patent: Apr. 30, 1996

[54] AZAAROMATIC COMPOUNDS, PROCESS FOR THEIR PREPARATION, AND THEIR USE IN LIQUID-CRYSTALLINE MIXTURES

[75] Inventors: Javier Manero, Frankfurt am Main; Hubert Schlosser, Glashütten/Taunus; Rainer Wingen, Hattersheim/Main, all of Germany

[73] Assignee: Hoechst Aktiengesellschaft, Frankfurt, Germany

[21] Appl. No.: 141,776

[22] Filed: Oct. 22, 1993

[30] Foreign Application Priority Data

Oct. 26, 1992 [DE] Germany .................. 42 36 106.0

[51] Int. Cl.$^6$ .................. C09K 19/34; C07D 401/04
[52] U.S. Cl. .................. 252/299.61; 544/238; 544/336; 544/405
[58] Field of Search .................. 252/299.61, 299.01; 544/238, 336, 405

[56] References Cited

U.S. PATENT DOCUMENTS

| | | | |
|---|---|---|---|
| 4,609,485 | 9/1986 | Kitano et al. | 252/299.61 |
| 4,668,425 | 5/1987 | Nigorikawa et al. | 252/299.61 |
| 5,204,477 | 4/1993 | Reiffenrath et al. | 546/303 |

FOREIGN PATENT DOCUMENTS

| | | |
|---|---|---|
| 0130790 | 11/1985 | European Pat. Off. |
| 0160790 | 11/1985 | European Pat. Off. |
| 4030603 | 9/1990 | Germany |
| 61-280489 | 11/1986 | Japan |
| 9211241 | 7/1992 | WIPO |
| WO92/12974 | 8/1992 | WIPO |

OTHER PUBLICATIONS

CA: 96:68926.
CA 106:50237.
CA 95:97829.

Japanese Abstract J6 1280-489-A.

Zaschke et al., Liquid Crystal Conference of Socialist Countries, 1987, "Preparation and Investigation of Liquid Crystalline Bis–Pyrimidines", p. E–8.

Primary Examiner—Shean C. Wu
Attorney, Agent, or Firm—Curtis, Morris & Safford

[57] ABSTRACT

Azaaromatic compounds of the formula I

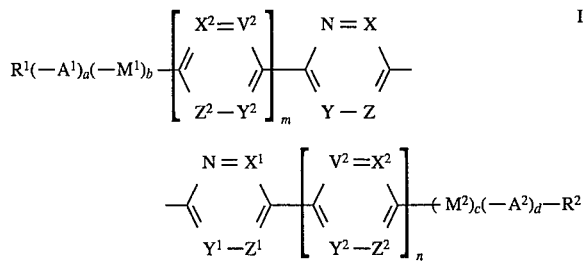

in which $R^1$ and $R^2$ are, for example, alkyl radicals, M is, for example, —O—, —COO— or —O—CO—O—, A is an aromatic or heteroaromatic ring, V, X, Y and Z are CH, CF or N, a,b,c,d,m and n are 0 or 1, where m+n is 0 or 1 and a+d is 0 or 1.

The compounds of the formula I are suitable as components of liquid-crystal mixtures.

5 Claims, No Drawings

AZAAROMATIC COMPOUNDS, PROCESS FOR THEIR PREPARATION, AND THEIR USE IN LIQUID-CRYSTALLINE MIXTURES

BACKGROUND OF THE INVENTION

Particularly in the last decade, liquid crystals have been introduced into various industrial areas in which electro-optical and display-device properties are required (for example in watch, calculator and typewriter displays). These display devices are based on dielectric alignment effects in the nematic, cholesteric and/or smectic phases of the liquid-crystalline compounds, where—caused by the dielectric anisotropy—the molecular long axis of the compounds adopts a preferential alignment in an applied electric field. The usual response times in these display devices are too long for many other potential areas of application of liquid crystals. This disadvantage is particularly noticeable if a large number of pixels must be addressed. Production costs of equipment containing relatively large screen areas, for example of video equipment, are then generally too high.

In addition to nematic and cholesteric liquid crystals, optically active smectic liquid crystals have also been increasing in importance over the last few years.

Clark and Lagerwall were able to show that the use of ferroelectric liquid-crystal systems in very thin cells results in electro-optical switching or display elements which have response times faster by a factor of 1000 compared with conventional TN ("twisted nematic") cells (cf., for example, Lagerwall et al., "Ferroelectric Liquid Crystals for Displays", SID Symposium, October Meeting 1985, San Diego, Calif., USA). On the basis of this and other favorable properties, for example the possibility of bistable switching and the virtually viewing angle-independent contrast, FLCs are in principle highly suitable for the abovementioned areas of application, for example via matrix addressing.

For electro-optical or fully optical components, either compounds are required which form tilted or orthogonal smectic phases and are themselves optically active, or ferroelectric smectic phases can be induced by doping compounds which, although forming such mectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved if the phase sequence of the liquid-crystal mixture is, with decreasing temperature:

isotropic→N*→$S_A$→$S^*_C$

The prerequisite is that the pitch of the helix in the N* phase is very large (greater than 10 µm) or even better is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved by adding a further optically active dope which induces a right-hand helix to the chiral liquid-crystal mixture which has, for example, a left-hand helix in the N* phase, in such amounts that the helix is just compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213–233 and 114 (1984), 151–187). As in the case of the cholesteric pitch, this is achieved by using dopes having the opposite rotation of the helix.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovxki in Advances in Liquid Crystal Research and Applications, Oxford/Budapest, 1980, 469 ff.; the PSFLCD effect is described in DE 3 920 625 and EP 0 405 346 A2. In contrast to the SSFLCD effect, utilization of these effects requires a liquid-crystalline material having a short $S_C$ pitch.

The optical response time τ [µs] of ferroelectric liquid-crystal systems, which should be as short as possible, depends on the rotational viscosity of the system γ[mPas], the spontaneous polarization $P_s$[nC/cm$^2$] and the electric field strength E[V/m], in accordance with the equation

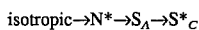

$$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably ≈0.13, and a low positive or preferably negative dielectric anisotropy Δε are required (see S. T. Lagerwall et al., "Ferroelectric Liquid Crystals for Displays", SID Symposium, October Meeting 1985, San Diego, Calif., USA).

The totality of these requirements can only be achieved by means of mixtures comprising a plurality of components. The base (or matrix) used preferably comprises compounds which if possible themselves already have the desired phase sequence I→N→$S_A$→$S_C$. Further components of the mixture are frequently added in order to reduce the melting point and to broaden the $S_C$ and usually also the N phase, to induce optical activity, for pitch compensation and to match the optical and dielectric anisotropy; further, the rotational viscosity, for example, should if possible not be increased.

Azaaromatic compounds have already been described as chiral and achiral components of liquid-crystalline mixtures. Thus, bispyrimidines have been described, for example, by M. Zaschke et al. (7th Liquid Crystal Conference of Socialist Countries, 1987, Pandurice, CSSR, E-8) and in EP-A 0 160 790, and pyridylpyrimidines have been described in U.S. Pat. No. 4,668,425, JP-A 61/280 489, DE-A 4 030 603 and WO 92/12974.

Since, however, the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

SUMMARY OF THE INVENTION

The object of the present invention was therefore to provide novel compounds which are suitable in liquid-crystalline mixtures for improving the property profile of these mixtures.

This object is achieved according to the invention by means of azaaromatic compounds of the formula I

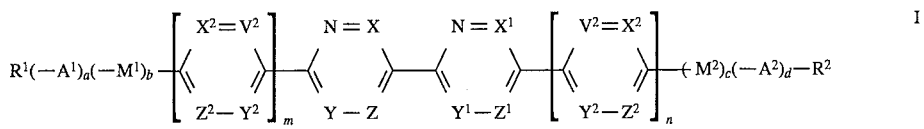

in which the symbols and indices have the following meanings:

$R^1$ and $R^2$ are, independently of one another, hydrogen or a straight-chain or branched alkyl radical having 1 to 20 carbon atoms (with or without asymmetrical carbon atoms), it also being possible for one or more $CH_2$ groups to be replaced by —O—, —S—, —CO—, —CS—, —CH=CH—, —C≡C—,

—Si(CH$_3$)$_2$—, 1,4-phenylene, trans-1,4-cyclohexylene or trans-1,3-cyclopentylene, with the proviso that oxygen atoms and sulfur atoms (referred to as chalcogens below) must not be bonded directly to one another, and/or one or more H atoms of the alkyl radical may be substituted by —F, —Cl, —Br, —$OR^3$, —SCN, —OCN or —$N_3$;

if $X^2$ and $Z^2$ are both simultaneously other than N, $R^1$ and $R^2$ may also be one of the following chiral groups:

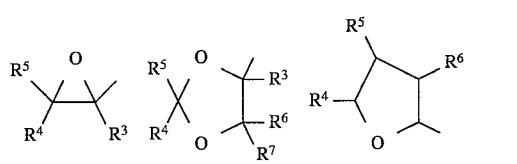

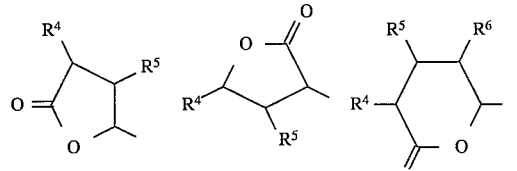

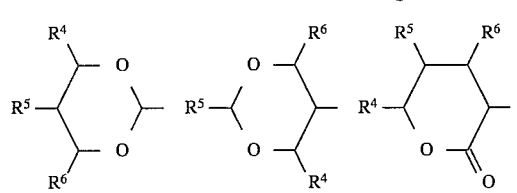

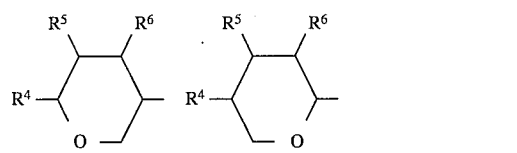

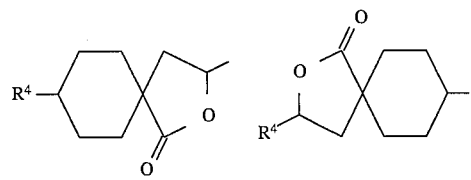

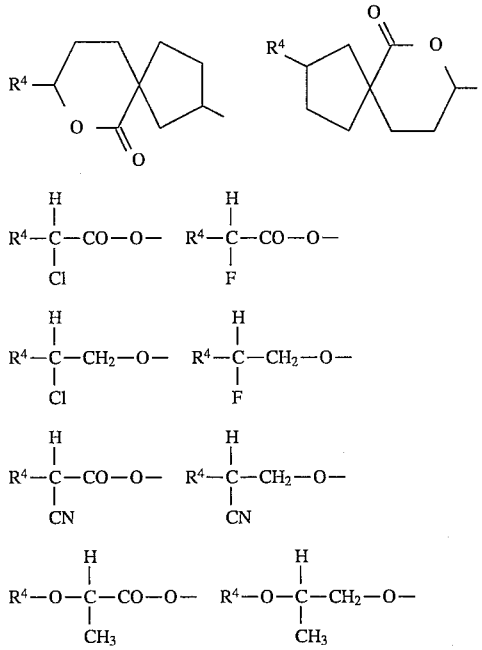

$R^3$, $R^4$, $R^5$, $R^6$ and $R^7$ are, independently of one another, hydrogen or a straight-chain or branched alkyl radical having 1–16 carbon atoms (with or without asymmetrical carbon atoms), it also being possible for one or more $CH_2$ groups to be replaced by —O— or —CH=CH—, with the proviso that oxygen atoms must not be bonded directly to one another, and/or one or more H atoms of the alkyl radical may be substituted by —F or —Cl; $R^4$ and $R^5$ together may also be —(CH$_2$)$_4$— or —(CH$_2$)$_5$— if they are bonded to an oxirane, dioxolane, tetrahydrofuran, tetrahydropyran, butyrolactone or valerolactone system;

X, Y, Z, $X^1$, $Y^1$, $Z^1$, $V^2$, $X^2$, $Y^2$ and $Z^2$ are, independently of one another, C—H, C—F or N;

$M^1$ and $M^2$ are, independently of one another, —O—, —S—, —CO—, —CO—O—, —O—CO—, —O—CO—O—, —CO—S—, —S—CO—, —CS—O—, —O—CS—, —S—CS—S—, —O—CS—O—, —S—CO—S—, —CS—, —CH$_2$—O—, —O—CH$_2$—, —CH$_2$—S—, —S—CH$_2$—, —CH=CH—, —C≡C— or a single bond;

$A^1$ and $A^2$ are, independently of one another, 1,4-phenylene, in which one or two H atoms may be replaced by F, Cl and/or CN, pyrazine-2,5-diyl, pyridazine-3,6-diyl, pyridine-2,5-diyl, pyrimidine-2,5-diyl, trans-1,4-cyclohexylene, in which one or two H atoms may be replaced by CN and/or CH$_3$, 1,3,4-thiadiazole-2,5-diyl, 1,3-dioxane-2,5-diyl, 1,3-dithiane-2,5-diyl, 1,3-thiazole-2,4-diyl, 1,3-thiazole-2,5-diyl, thiophene-2,4-diyl, thiophene-2,5-diyl, piperazine-1,4-diyl, piperazine-2, 5-diyl, naphthalene-2,6-diyl, bicyclo[2.2.2]octane-1,4-diyl or 1,3-di-oxaborinane-2,5-diyl;

a, b, c, d, m and n are zero or one, with the proviso that the sum m+n is 0 or 1 and the sum a+d is 0 or 1, with the exception of compounds in which the

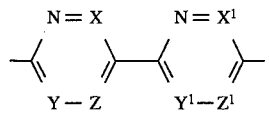

group has the following meaning:

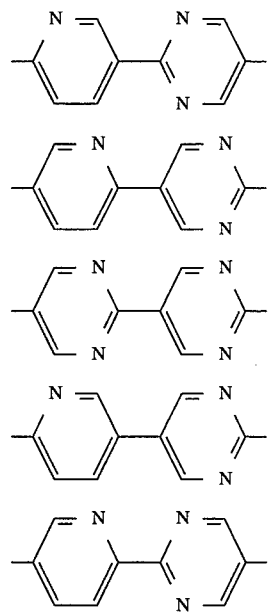

DESCRIPTION OF THE PREFERRED EMBODIMENTS

Preference is given to compounds of the formula I in which the symbols and indices have the following meanings, with retention of the above-described exceptions:

$R^1$ and $R^2$ are, independently of one another, hydrogen or a straight-chain or branched alkyl radical having 1 to 18 carbon atoms (with or without asymmetrical carbon atoms), it also being possible for one or more $CH_2$ groups to be replaced by —O—, —CO—, —CH=CH—, —C≡C—,

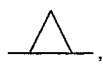

—Si(CH$_3$)$_2$— or trans-1,4-cyclohexylene, with the proviso that oxygen atoms must not be bonded directly to one another, and/or one or more H atoms of the alkyl radical may be substituted by —F, —Cl, —OR$^3$, —OCN or —N$_3$;

if $X^2$ and $Z^2$ are both simultaneously other than N, $R^1$ and $R^2$ may also be one of the following chiral groups:

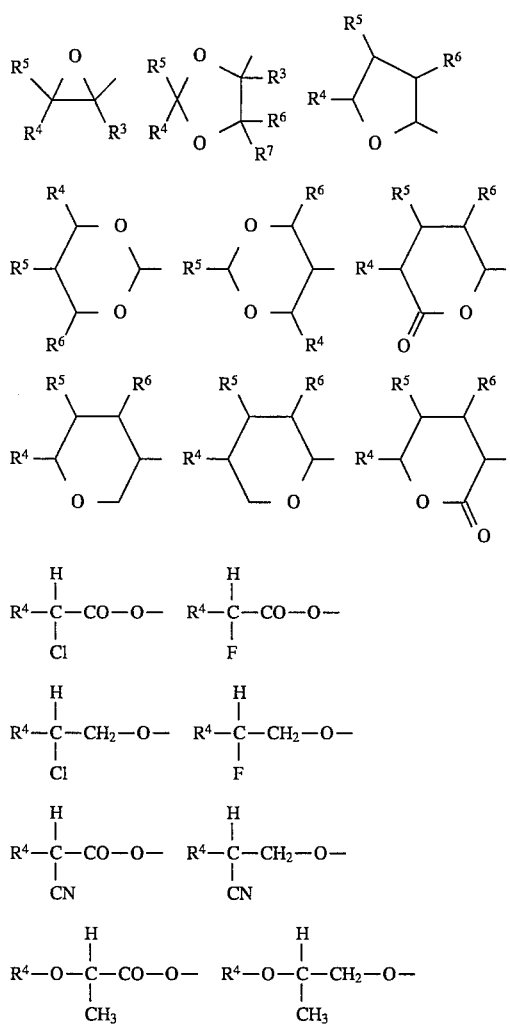

$R^3$, $R^4$, $R^5$, $R^6$ and $R^7$ are, independently of one another, hydrogen or a straight-chain or branched alkyl radical having 1–16 carbon atoms (with or without asymmetrical carbon atoms), it also being possible for one or more $CH_2$ groups to be replaced by —O— or —CH=CH—, with the proviso that oxygen atoms must not be bonded directly to one another, and/or one or more H atoms of the alkyl radical may be substituted by —F or —Cl; $R^4$ and $R^5$ together may also be —(CH$_2$)$_4$— or —(CH$_2$)$_5$— if they are bonded to an oxirane, dioxolane, tetrahydrofuran, tetrahydropyran, butyrolactone or valerolactone system;

X, Y, Z, $X^1$, $Y^1$, $Z^1$, $V^2$, $X^2$, $Y^2$ and $Z^2$ are, independently of one another, C—H, C—F or N;

$M^1$ and $M^2$ are, independently of one another, —O—, —CO—, —CO—O—, —O—CO—, —O—CO—O—, —O—CS—O—, —CH$_2$—O—, —O—CH$_2$—, —CH=CH—, —C≡C— or a single bond;

$A^1$ and $A^2$ are, independently of one another, 1,4-phenylene, in which one or two H atoms may be replaced by F, Cl and/or CN, pyrazine-2,5-diyl, pyridazine-3,6-diyl, pyridine-2,5-diyl, pyrimidine-2,5-diyl, trans-1,4-cyclohexylene, in which one or two H atoms may be replaced by CN and/or CH$_3$, 1,3,4-thiadiazole-2,5-diyl, 1,3-dioxane-2,5-diyl, thiophene-2,4-diyl, thiophene-2,5-diyl, naphthalene-2,6-diyl or 1,3-dioxaborinane-2,5-diyl;

a, b, c, d, m and n are zero or one, with the proviso that the sum m+n is 0 or 1 and the sum a+d is 0 or 1.

Particular preference is given to compounds of the formula I in which the symbols and indices have the following meanings, with retention of the above-described exceptions:

$R^1$ and $R^2$ are, independently of one another, hydrogen or a straight-chain or branched alkyl radical having 1 to 16 carbon atoms (with or without asymmetrical carbon atoms), it also being possible for one, two or three $CH_2$ groups to be replaced by —O—, —CO—, —CH=CH—,

—Si(CH$_3$)$_2$— or trans-1,4-cyclohexylene, with the proviso that oxygen atoms must not be bonded directly to one another, and/or one or more H atoms of the alkyl radical may be replaced by —F, —Cl or —OR$^3$;

if $X^2$ and $Z^2$ are both simultaneously other than N, $R^1$ and $R^2$ may also be one of the following chiral groups:

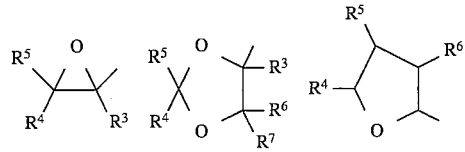

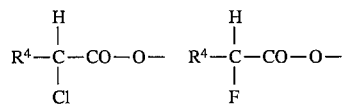

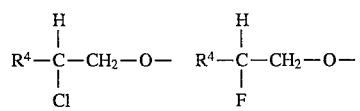

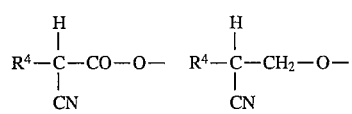

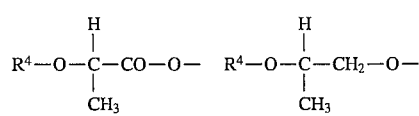

$R^3$, $R^4$, $R^5$, $R^6$ and $R^7$ are, independently of one another, hydrogen or a straight-chain or branched alkyl radical having 1–14 carbon atoms (with or without asymmetrical carbon atoms), it also being possible for one or more $CH_2$ groups to be replaced by —O— or —CH=CH—, with the proviso that oxygen atoms must not be bonded directly to one another, and/or one or more H atoms of the alkyl radical may be substituted by — F or —Cl; $R^4$ and $R^5$ together may also be —(CH$_2$)$_4$— or —(CH$_2$)$_5$— if they are bonded to an oxirane or dioxolane system;

X, Y, Z, $X^1$, $Y^1$, $Z^1$, $V^2$, $X^2$, $Y^2$ and $Z^2$ are, independently of one another, C—H, C—F or N;

$M^1$ and $M^2$ are, independently of one another, —O—, —CO—, —CO—O—, —O—CO—, —O—CO—O—, —CH$_2$—O—, —O—CH$_2$—, —CH=CH— or a single bond;

$A^1$ and $A^2$ are, independently of one another, 1,4-phenylene, in which one or two H atoms may be replaced by F, Cl and/or CN, pyrazine-2,5-diyl, pyridazine-3,6-diyl, pyridine-2,5-diyl, pyrimidine-2,5-diyl, trans-1,4-cyclohexylene, in which one or two H atoms may be replaced by CN and/or CH$_3$, 1,3,4-thiadiazole-2,5-diyl, naphthalene-2,6-diyl or 1,3-dioxaborinane-2,5-diyl;

a, b, c, d, m and n are zero or one, with the proviso that the sum m+n is 0 or 1 and the sum a+d is 0or 1.

Very particular preference is given to compounds of the formula I in which the symbols and indices have the following meanings, with the retention of the above-described exceptions in which the

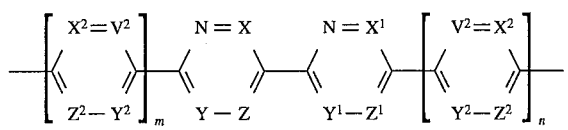

group has the following meaning:

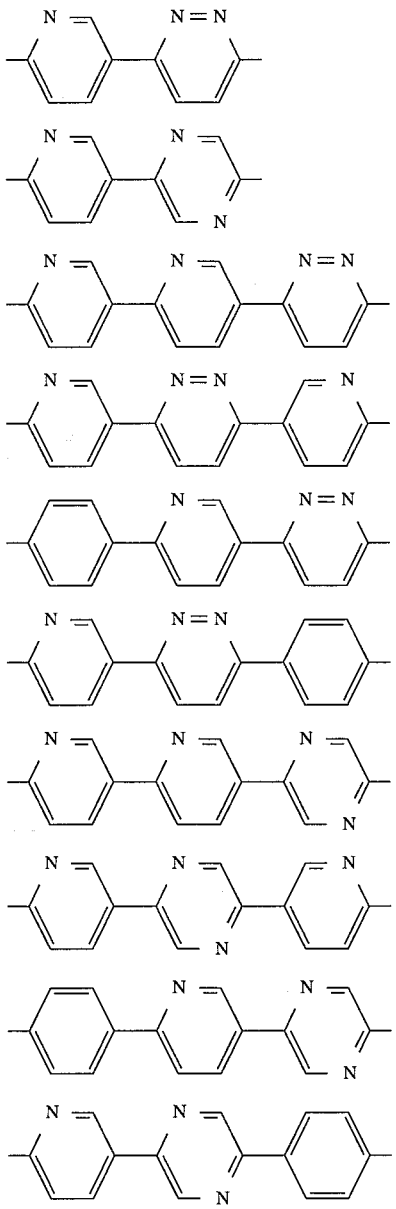

$R^1$ and $R^2$ are, independently of one another, hydrogen or a straight-chain or branched alkyl radical having 1 to 16 carbon atoms (with or without asymmetrical carbon atoms), it also being possible for one, two or three $CH_2$ groups to be replaced by —O—, —CO—, —CH=CH—,

—Si(CH$_3$)$_2$— or trans-1,4-cyclohexylene, with the proviso that oxygen atoms must not be bonded directly to one another, and/or one or more H atoms of the alkyl radical may be substituted by —F or —OR$^3$;

if $X^2$ and $Z^2$ are both simultaneously other than N, $R^1$ and $R^2$ may also be one of the following chiral groups:

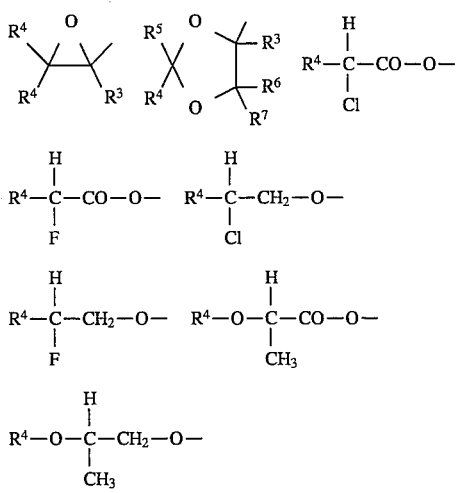

$R^3$, $R^4$, $R^5$, $R^6$ and $R^7$ are, independently of one another, hydrogen or a straight-chain or branched alkyl radical having 1–10 carbon atoms (with or without asymmetrical carbon atoms), it also being possible for one or two $CH_2$ groups to be replaced by —O— or —CH=CH—, with the proviso that oxygen atoms must not be bonded directly to one another, and/or one or more H atoms of the alkyl radical may be substituted by —F or —Cl; $R^4$ and $R^5$ together may also be —(CH$_2$)$_4$— or —(CH$_2$)$_5$— if they are bonded to an oxirane or dioxolane system;

X, Y, Z, $X^1$, $Y^1$, $Z^1$, $V^2$, $X^2$, $Y^2$ and $Z^2$ are, independently of one another, C—H, C—F or N;

$M^1$ and $M^2$ are, independently of one another, —O—, —CO—, —CO—O—, —O—CO—, —O—CO—O—, —CH$_2$—O—, —O—CH$_2$— or a single bond;

$A^1$ and $A^2$ are, independently of one another, 1,4-phenylene, in which one or two H atoms may be replaced by F, Cl and/or CN, pyrazine-2,5-diyl, pyridazine-3,6-diyl, pyridine-2,5-diyl, pyrimidine-2,5-diyl, trans-1,4-cyclohexylene, in which one or two H atoms may be replaced by CN and/or $CH_3$, 1,3,4-thiadiazole-2,5-diyl or naphthalene-2,6-diyl;

a, b, c, d, m and n are zero or one, with the proviso that the sum m+n is 0 or 1 and the sum a+d is 0 or 1.

The compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use may also be made here of variants which are known per se but not mentioned in greater detail here.

For example, reference is made to DE-A 23 44 732, 24 50 088, 24 29 093, 25 02 904, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; N. Miyaura, T. Yanagi and A. Suzuki in Synthetic Communications 11 (1981), pp. 513–519, DE-C 3 930 663, M. J. Sharp, W. Cheng, V. Snieckus in Tetrahedron Letters 28 (1987), p. 5093 ff.; G. W. Gray in J. Chem. Soc. Perkin Trans. II, 1989, p. 2041 ff. and Mol. Cryst. Sig. Cryst. 172 (1989), p. 165 ff., 204 (1991), p. 43 ff. and p. 91 ff.; EP-A 0 449 015; WO 89/12039; WO 89/03821; EP-A 0 354 434 for the direct linking of aromatic and heteroaromatic compounds; WO 92/08714 for the direct linking of nitrogen-containing heteroaromatic compounds to nitrogen-containing heteroaromatic compounds; DE-A 32 01 721 for compounds containing —CH$_2$CH$_2$— bridges, and Koji Seto et al. in Liquid Crystals 8 (1990), pp. 861–870 for compounds containing —C≡C— bridges.

The preparation of disubstituted pyridines, disubstituted pyrazines, disubstituted pyrimidines and disubstituted pyridazines is described, for example, in the appropriate volumes of the series "The Chemistry of Heterocyclic Compounds" by A. Weissberger and E. C. Taylor (editors).

The preparation of alkyl-substituted heterocyclic compounds is described, for example, in "Comprehensive Organometallic Chemistry", Vol. 8 (1982 edition) by G. Wilkinson, F. G. A. Stone and E. W. Abel (editors).

If desired, the starting materials can also be prepared in situ by not isolating them from the reaction mixture, but instead immediately converting them further into the compounds of the formula (I).

In a preferred process for the preparation of compounds of the formula I, an organometallic compound of the formula Ia

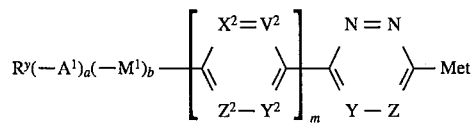

in which $A^1$, $M^1$, X, $X^2$, V, $V^2$, Z, $Z^2$, Y, $Y^2$, a, b and m are as defined under formula I, $R^y$ is identical to $R^1$ or is a suitably protected derivative of $R^1$ which can be converted thereto in a later step, and Met is Li, Na, K, MgG, ZnG, B(G)$_2$, Al(G)$_3$, Ti(G)$_3$, Zr(G)$_3$, HgG or SnG$_3$, in which G is in each case, independent of one another, halogen, alkyl or alkoxy, in each case having 1 to 6 carbon atoms, or is a cyclopentadienyl radical, it also being possible for G to be OH in the case where Met is B(G)$_2$, is coupled with a compound of the formula Ib

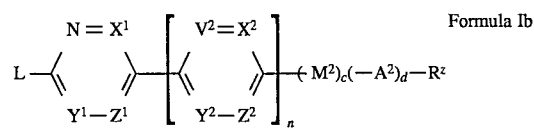

Formula Ib in which $A^2$, $M^2$, V, X, Y, Z, $V^2$, $X^2$, $Y^2$, $Z^2$, n, c and d are as defined under formula I, $R^z$ is identical to $R^2$ or is a suitably protected derivative of $R^2$ which can be converted thereto in a later step, and L is halogen or OSO$_2$—C$_k$F$_{2k+1}$, in which k is an integer from 1 to 10, in an inert solvent at a temperature of from −78° C. to 200° C. with transition-metal catalysis.

The catalyst used is preferably palladium or a palladium compound. The solvents used are, for example, ethers and hydrocarbons.

The synthesis of the precursors Ia and Ib is illustrated in greater detail in schemes A to E below.

Scheme A

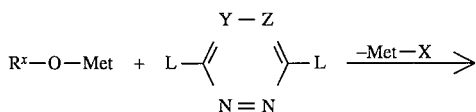

(I)

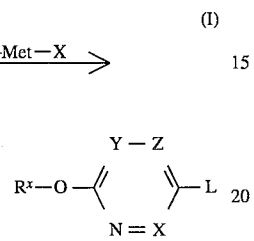

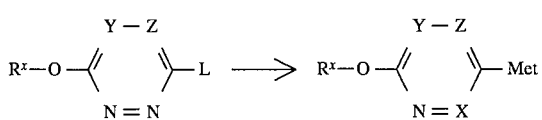

(II)

X, Y, Z = C−H, C−F, N

Scheme B

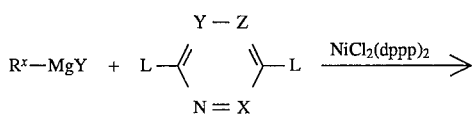

(I)

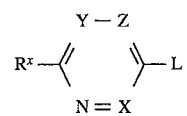

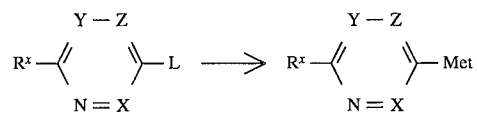

(II)

X, Y, Z = C−H, C−F, N

Scheme C

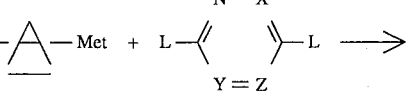

(I)

(II)

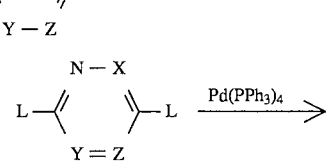

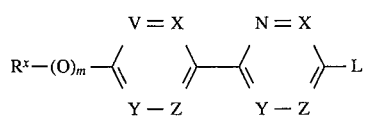

(III)

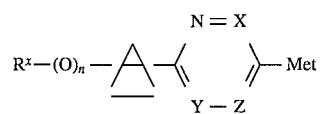

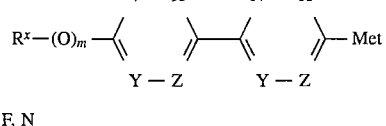

(IV)

V, X, Y, Z = C−H, C−F, N
n, m = 0, 1

Scheme D

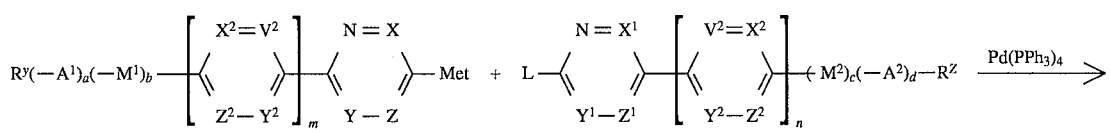

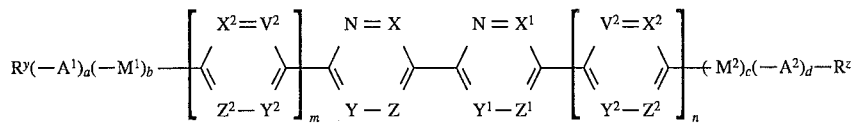

$R^x$ in the above schemes is as defined for $R^y$ or $R^z$.

Scheme E

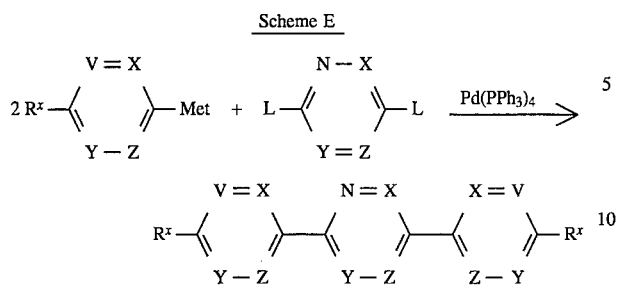

V, X, Y, Z = C—H, C—F, N

A in scheme C is as defined for $A^1$ in the formula I. The substances obtained in accordance with scheme C can in turn be employed as starting materials for the reactions described under scheme C.

According to scheme E, tricyclic liquid crystals in which the outer rings and the wing groups are identical can be obtained, for example, in a single step.

Particularly preferred processes for the preparation of the compounds according to the invention are proposed in German Patent Applications P 4236103.6 "Process for the cross-coupling of aromatic boronic acids with aromatic halogen compounds or perfluoroalkyl sulfonates", P 4236105.2 "Arylboronic acids as precursors for the preparation of components of liquid-crystal mixtures" and P 4236104.4 "Bifunctional precursors for the preparation of liquid crystals".

In these processes, aromatic boronic acids are reacted with aromatic halo- or aromatic perfluoroalkyl sulfonates in the presence of a base, catalytic amounts of metallic palladium and catalytic amounts of a ligand, for example a phosphine, to give polycyclic aromatic compounds.

Another particularly preferred process is described in WO 92/08714.

Said azaaromatic compounds are suitable as components of liquid-crystal (LC) mixtures, preferably of those comprising 2 to 20 compounds. The LC mixtures here may contain from 0.01 to 80% by weight, preferably from 0.1 to 60% by weight, particularly preferably from 0.1 to 30% by weight, of one or more, preferably from 1 to 10, particularly preferably from 1 to 5, of the compounds according to the invention.

The other constituents are advantageously selected from known compounds having nematic, cholesteric and/or smectic phases. These include, for example:

derivatives of phenylpyrimidine, as described, for example, in WO 86/06401 and U.S. Pat. No. 4 874 542, meta-substituted six-membered aromatic compounds, as described, for example, in German Patent Application P 4 222 565, silicon compounds, as described, for example, in EP-A 0 355 008, hydroquinone derivatives, as described, for example, in German Patent Application P 4 243 705, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and macrocyclic compounds, as described, for example, in EP-A 0 528 415.

Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and DE P 4 143 139, optically active oxirane esters, as described, for example, in EP-A 0 292 954, optically active dioxolane ethers, as described, for example, in EP-A 0 351 746, optically active dioxolane esters, as described, for example, in EP-A 0 361 272, and optically active tetrahydrofuran-2-carboxylic esters, as described, for example, in EP-A 0 355 561.

The compounds according to the invention are preferably used in ferroelectric LC mixtures.

The compounds of the formula I have a broad range of applications. Depending on the choice of substituents, these compounds can be used as base materials from which liquid-crystalline, smectic, in particular ferroelectric, phases are predominantly composed; however, it is also possible to add compounds of the formula I to liquid-crystalline base materials from other classes of compound in order, for example, to vary the dielectric and/or optical anisotropy and/or the viscosity and/or the spontaneous polarization and/or the phase ranges and/or the tilt angle and/or the pitch of a dielectric of this type.

The mixtures according to the invention can in turn be used in electro-optical or fully optical elements, for example display elements, switching elements, light modulators, elements for image processing and/or signal processing or generally in the area of nonlinear optics.

Electro-optical display elements whose liquid-crystalline mixtures contain compounds of the formula I additionally contain, for example, the following components: two electrodes, two carrier plates and at least one alignment layer. In general, the structure of FLC displays is described, for example, in EP-B 0 032 362.

The present invention is described in greater detail with reference to the Examples below:

EXAMPLE 1

Preparation of precursors in accordance with scheme A-I
3-Chloro-6-octyloxypyridazine 106.7 ml of 1-octanol in 400 ml of THF or DMF are added dropwise over the course of 40 minutes to 24.19 g of sodium hydride (80% in mineral oil) in 200 ml of tetrahydrofuran (THF) or dimethylformamide (DMF). A solution of 100 g of 3,6-dichloropyridazine in 300 ml of THF or DMF is subsequently added dropwise. The mixture is stirred for a further 6 hours and heated if necessary, 1.6 l of saturated ammonium chloride solution are added, the organic phase is separated off, and the water phase is extracted with tert-butyl methyl ether. The combined organic phases are dried, and the solvent is removed in vacuo. The crude product can be purified by chromatography or by distillation (0.8 mm Hg/141° C.).

Yield: 88 g

The starting materials listed below can be converted into the corresponding products analogously to this procedure. In addition to octanol, the following alcohol components, inter alia, can also be employed: 3-oxapentanol, 3-oxahexanol, 4-oxahexanol, 3-oxaheptanol, 4-oxaheptanol, 5-oxaheptanol, 3-oxaoctanol, 4-oxaoctanol, 5-oxaoctanol, 6-oxaoctanol, 3-oxanonanol, 4-oxanonanol, 5-oxanonanol, 6-oxanonanol, 7-oxanonanol, 3-oxadecanol, 4-oxadecanol, 5-oxadecanol, 6-oxadecanol, 7-oxadecanol, 8-oxadecanol, 3-oxaundecanol, 4-oxaundecanol, 5-oxaundecanol, 6-oxaundecanol, 7-oxaundecanol, 8-oxaundecanol, 9-oxaundecanol, 3-oxadodecanol, 4-oxadodecanol, 5-oxadodecanol, 6-oxadodecanol, 7-oxadodecanol, 8-oxadodecanol, 9-oxadodecanol, 10-oxadodecanol, 3-oxatridecanol, 4-oxatridecanol, 5-oxatridecanol, 6-oxatridecanol, 7-oxatridecanol, 8-oxatridecanol, 9-oxatridecanol, 10-oxatridecanol, 11-oxatridecanol, 3-oxatetradecanol, 4-oxatetradecanol, 5-oxatetradecanol, 6-oxatetradecanol, 7-oxatetradecanol, 8-oxatetradecanol, 9-oxatetradecanol, 10-oxatetradecanol, 11-oxatetradecanol, 12-oxatetradecanol, 3-dimethylsilapentanol, 3-dimethylsilahexanol, 4-dimethylsilahexanol, 3-dimethylsilaheptanol, 4-dimethylsilaheptanol, 5-dimethylsilaheptanol, 3-dimethylsilaoctanol, 4-dimethylsilaoctanol, 5-dimethylsilaoctanol, 6-dimethylsilaoctanol, 3-dimethylsilanonanol, 4-dimethylsilanonanol, 5-dimethylsilanonanol, 6-dimethylsilanonanol, 7-dimethylsilanonanol, 3-dimethylsiladecanol, 4-dimethylsiladecanol, 5-dimethylsiladecanol, 6-dimethylsiladecanol, 7-dimethylsiladecanol, 8-dimethylsiladecanol, 3-dimethylsilaundecanol, 4-dimethylsilaundecanol, 5-dimethylsilaundecanol, 6-dimethylsilaundecanol, 7-dimethylsilaundecanol, 8-dimethylsilaundecanol, 9-dimethylsilaundecanol, 3-dimethylsiladodecanol, 4-dimethylsiladodecanol, 5-dimethylsiladodecanol, 6-dimethylsiladodecanol, 7-dimethylsiladodecanol, 8-dimethylsiladodecanol, 9-dimethylsiladodecanol, 10-dimethylsiladodecanol, 3-dimethylsilatridecanol, 4-dimethylsilatridecanol, 5-dimethylsilatridecanol, 6-dimethylsilatridecanol, 7-dimethylsilatridecanol, 8-dimethylsilatridecanol, 9-dimethylsilatridecanol, 10-dimethylsilatridecanol, 11-dimethylsilatridecanol, 3-dimethylsilatetradecanol, 4-dimethylsilatetradecanol, 5-dimethylsilatetradecanol, 6-dimethylsilatetradecanol, 7-dimethylsilatetradecanol, 8-dimethylsilatetradecanol, 9-dimethylsilatetradecanol, 10-dimethylsilatetradecanol, 11-dimethylsilatetradecanol, 12-dimethylsilatetradecanol, perfluoro-1H,1H-ethanol, perfluoro-1H,1H-propanol, perfluoro-1H,1H-butanol, perfluoro-1H,1H-pentanol, perfluoro-1H,1H-hexanol, perfluoro-1H,1H-heptanol, perfluoro-1H,1H-octanol, perfluoro-1H,1H-nonanol, perfluoro-1H,1H-decanol, perfluoro-1H,1H-undecanol, perfluoro-1H,1H-dodecanol, perfluoro-1H,1H-tridecanol, perfluoro-1H,1H-tetradecanol and perfluoro-1H,1H-pentadecanol.

In addition to 3,6-dichloropyridazine, the following heteroaromatic components, inter alia, can also be employed:

3,6-dibromopyridazine, 2,5-dibromopyridine, 2,5-dichloropyridine, 2,5-dibromopyrazine, 2,5-dichloropyrazine, 2-fluoro-3,6-dibromopyridine, 2-fluoro-3,6-dichloropyridine, 3-fluoro-2,5-dibromopyridine and 3-fluoro-2,5-dichloropyridine.

EXAMPLE 2

Preparation of precursors in accordance with scheme B-I
2-Octyl-5-bromopyridine 30 mmol of n-octylmagnesiumbromide in 50 ml of absolute THF are added dropwise at from −15° to −10° C. to a solution of 5 g (21.1 mmol) of dibromopyridine and 0.12 g of [1,3-bis(diphenylphosphino)propane]nickel (II) chloride in 150 ml of absolute THF. The mixture is stirred at −10° C. for a further 3 hours. Saturated $NH_4Cl$ solution is subsequently added until a pH of 7 has become established, and $CH_2Cl_2$ is added for phase separation. The organic phase is separated off, the aqueous phase is extracted three times with $CH_2Cl_2$, the combined organic phases are dried over $MgSO_4$, and the solvent is stripped off in a rotary evaporator.

The crude product is chromatographed on $SiO_2$ using $CH_2Cl_2$.

Yield: 1.67 g

The starting materials listed below can be converted into the corresponding products analogously to this procedure. In addition to the octyl Grignard compound, the following Grignard reagents, inter alia, can also be employed: 3-oxapentyl Grignard compound, 3-oxahexyl Grignard compound, 4-oxahexyl Grignard compound, 3-oxaheptyl Grignard compound, 4-oxaheptyl Grignard compound, 5oxaheptyl Grignard compound, 3-oxaoctyl Grignard compound, 4-oxaoctyl Grignard compound, 5-oxaoctyl Grignard compound, 6-oxaoctyl Grignard compound, 3-oxanonyl Grignard compound, 4-oxanonyl Grignard compound, 5-oxanonyl Grignard compound, 6-oxanonyl Grignard compound, 7-oxanonyl Grignard compound, 3-oxadecyl Grignard compound, 4-oxadecyl Grignard compound, 5-oxadecyl Grignard compound, 6-oxadecyl Grignard compound, 7-oxadecyl Grignard compound, 8-oxadecyl Grignard compound, 3-oxaundecyl Grignard compound, 4-oxaundecyl Grignard compound, 5-oxaundecyl Grignard compound, 6-oxaundecyl Grignard compound, 7-oxaundecyl Grignard compound, 8-oxaundecyl Grignard compound, 9-oxaundecyl Grignard compound, 3-oxadodecyl Grignard compound, 4-oxadodecyl Grignard compound, 5-oxadodecyl Grignard compound, 6-oxadodecyl Grignard compound, 7-oxadodecyl Grignard compound, 8-oxadodecyl Grignard compound, 9-oxadodecyl Grignard compound, 10-oxadodecyl Grignard compound, 3-oxatridecyl Grignard compound, 4-oxatridecyl Grignard compound, 5-oxatridecyl Grignard compound, 6-oxatridecyl Grignard compound, 7-oxatridecyl Grignard compound, 8-oxatridecyl Grignard compound, 9-oxatridecyl Grignard compound, 10-oxatridecyl Grignard compound, 11-oxatridecyl Grignard compound, 3-oxatetradecyl Grignard compound, 4-oxatetradecyl Grignard compound, 5-oxatetradecyl Grignard compound, 6-oxatetradecyl Grignard compound, 7-oxatetradecyl Grignard compound, 8-oxatetradecyl Grignard compound, 9-oxatetradecyl Grignard compound, 10-oxatetradecyl Grignard compound, 11-oxatetradecyl Grignard compound, 12-oxatetradecyl Grignard compound, 3-dimethylsilapentyl Grignard compound, 3-dimethylsilahexyl Grignard compound, 4-dimethylsilahexyl Grignard compound, 3-dimethylsilaheptyl Grignard compound, 4-dimethylsilaheptyl Grignard compound, 5-dimethylsilaheptyl Grignard compound, 3-dimethylsilaoctyl Grignard compound, 4-dimethylsilaoctyl Grignard compound, 5-dimethylsilaoctyl Grignard compound, 6-dimethylsilaoctyl Grignard compound, 3-dimethylsilanonyl Grignard compound, 4-dimethylsilanonyl Grignard compound, 5-dimethylsilanonyl Grignard compound, 6-dimethylsilanonyl Grignard compound, 7-dimethylsilanonyl Grignard compound, 3-dimethylsiladecyl Grignard compound, 4-dimethylsiladecyl Grignard compound, 5-dimethylsiladecyl Grignard compound, 6-dimethylsiladecyl Grignard compound, 7-dimethylsiladecyl Grignard compound, 8-dimethylsiladecyl Grignard compound, 3-dimethylsilaundecyl Grignard compound, 4-dimethylsilaundecyl Grignard compound, 5-dimethylsilaundecyl Grignard compound, 6-dimethylsilaundecyl Grignard compound, 7-dimethylsilaundecyl Grignard compound, 8-dimethylsilaundecyl Grignard compound, 9-dimethylsilaundecyl Grignard compound, 3-dimethylsiladodecyl Grignard compound, 4-dimethylsiladodecyl Grignard compound, 5-dimethylsiladodecyl Grignard compound, 6-dimethylsiladodecyl Grignard compound, 7-dimethylsiladodecyl Grignard compound, 8-dimethylsiladodecyl Grignard compound, 9-dimethylsiladodecyl Grignard compound, 10-dimethylsiladodecyl Grignard compound, 3-dimethylsilatridecyl Grignard compound, 4-dimethylsilatridecyl Grignard compound, 5-dimethylsilatridecyl Grignard compound, 6-dimethylsilatridecyl Grignard compound, 7-dimethylsilatridecyl Grignardnnnnnn compound, 8-dimethylsilatridecyl Grignard compound, 9-dimethylsilatridecyl Grignard compound, 10-dimethylsilatridecyl Grignard compound, 11-dimethylsilatridecyl Grignard compound, 3-dimethylsilatetradecyl Grignard compound, 4-dimethylsilatetradecyl Grignard compound, 5-dimethylsilatetradecyl Grignard compound, 6-dimethylsilatetradecyl Grignard compound, 7-dimethylsilatetradecyl Grignard compound, 8-dimethylsilatetradecyl Grignard compound, 9-dimethylsilatetradecyl Grignard compound, 10-dimethylsilatetradecyl Grignard compound, 11-dimethylsilatetradecyl Grignard compound, 12-dimethylsilatetradecyl Grignard compound, methyl Grignard compound, ethyl Grignard compound, propyl Grignard compound, butyl Grignard compound, pentyl Grignard compound, hexyl Grignard compound, heptyl Grignard compound, nonyl Grignard compound, decyl Grignard compound, undecyl Grignard compound, dodecyl Grignard compound, tridecyl Grignard compound and tetradecyl Grignard compound.

In addition to 3,6-dichloropyridazine, the following heteroaromatic components, inter alia, can also be employed:

3,6-dibromopyridazine, 2,5-dibromopyridine, 2,5-dichloropyridine, 2,5-dibromopyrazine, 2,5-dichloropyrazine, 2-fluoro-3,6-dibromopyridine, 2-fluoro-3,6-dichloropyridine, 3-fluoro-2,5-dibromopyridine and 3-fluoro-2,5dichloropyridine.

EXAMPLES 3a to 3c

Preparation of precursors in accordance with scheme A-II and/or B-II

In general, intermediates A-II and B-II can be isolated. They are then prepared in accordance with procedure 3a. In certain cases in which the groups Z and/or X are C—F or N, the intermediates A-II and B-II prove to be water-sensitive and therefore cannot be obtained in accordance with procedure 3a. In this case, they are synthesized by procedure 3aa and further converted in situ by reaction C-II. The above applies analogously to reactions C-III and C-IV.

EXAMPLE 3a

2-Octyloxy-5-pyridineboronic acid 15 g (52.5 mmol) of 2-octyloxy-5-bromopyridine are dissolved in 150 ml of absolute diethyl ether under a protective gas, and the solution is subsequently cooled to 0° C. 32.8 ml (52.5 mmol) of 1.6 molar n-butyllithium solution in hexane are added dropwise over the course of 15 minutes. The mixture is stirred at 0° C. for a further hour. 7.2 ml (63.2 mmol) of trimethyl borate are then added dropwise, the mixture is allowed to warm to room temperature and is then stirred for a further 1 hour, and 78 ml of 5% strength by weight aqueous HCl solution are then added dropwise over the course of 15 minutes. The mixture is stirred for a further hour. For work-up, the phases are separated, and the aqueous phase is extracted twice with diethyl ether and a further two times with dichloromethane. The combined organic phases are dried over magnesium sulfate. Removal of the solvent gives the product as a viscous, reddish oil.

Yield: 12.7 g

EXAMPLE 3b

2-Heptyl-5-pyridineboronic acid
Analogously to Example 3a from 2-heptyl-5-bromopyridine

EXAMPLE 3c 2-(6-Cyclopropylhexoxy)-5-pyridineboronic acid
Analogously to Example 3a from 2-(6-cyclopropylhexoxy)-5-bromopyridine

EXAMPLE 3d 2-(9-Cyclopropylnonyl )-5-pyridineboronic acid
Analogously to Example 3a from 2-(9-cyclopropylnonyl)-5bromopyridine

EXAMPLE 3e 2-(3-Oxapentoxy)-5-pyridineboronic acid
Analogously to Example 3a from 2-(3-oxapentoxy)-5-bromo-pyridine

EXAMPLE 3f 2-(5-Oxaundecyl)-5-pyridineboronic acid
Analogously to Example 3a from 2-(5-oxaundecyl)-5-bromo-pyridine

EXAMPLE 3 g 2-(3-Dimethylsilanonyloxy)-5-pyridineboronic acid
Analogously to Example 3a from 2-(3-dimethylsilanonyloxy)-5-bromopyridine

EXAMPLE 3h 2-(5-Dimethylsiladecyl)-5-pyridineboronic acid
Analogously to Example 3a from 2-(5-dimethylsiladecyl)-5-bromopyridine

EXAMPLE 3i 2-(Perfluoro-1H,1H-nonyloxy)-5-pyridineboronic acid
Analogously to Example 3a from 2-(perfluoro-1H,1H-nonyloxy)-5-bromopyridine

EXAMPLE 3aa

3-Octyloxy-6-pyridazineboronic acid
17.1 g (70.6 mmol) of 3-octyloxy-6-chloropyridazine are dissolved in 100 ml of absolute THF and cooled to −78° C. under a protective gas. 47.1 ml (75.2 mmol) of 1.6 molar n-butyllithium solution in hexane are then added dropwise over the course of 30 minutes. The mixture is stirred at −78° C. for a further 30 minutes. 216 ml (215.7 mmol) of 1.0 molar $ZnCl_2$ solution in diethyl ether are subsequently slowly added dropwise, during which the temperature must not exceed −60° C. When the addition is complete, the mixture is stirred for a further 30 minutes. The crude boronic acid is employed directly, without isolation from the solution, for the subsequent couplings.

EXAMPLE 3ab

2-Heptyl-5-pyridazineboronic acid
Analogously to Example 3aa from 2-heptyl-5-bromopyridazine

EXAMPLE 3ac 2-(6-Cyclopropylhexoxy)-5-pyridazineboronic acid
Analogously to Example 3aa from 2-(6-cyclopropylhexoxy)-5-bromopyridazine

EXAMPLE 3ad 2-(9-Cyclopropylnonyl)-5-pyridazineboronic acid
Analogously to Example 3aa from 2-(9-cyclopropylnonyl)-5-bromopyridazine

EXAMPLE 3ae 2-(3-Oxapentoxy)-5-pyridazineboronic acid
Analogously to Example 3aa from 2-(3-oxapentoxy)-5-bromopyridazine

EXAMPLE 3af 2-(5-Oxaundecyl)-5-pyridazineboronic acid
Analogously to Example 3aa from 2-(5-oxaundecyl)-5-bromopyridazine

EXAMPLE 3ag 2-(3-Dimethylsilanonyloxy)-5-pyridazineboronic acid
Analogously to Example 3aa from 2-(3-dimethylsilanonyloxy)-5-bromopyridazine

EXAMPLE 3ah 2-(5-Dimethylsiladecyl)-5-pyridazineboronic acid
Analogously to Example 3aa from 2-(5-dimethylsiladecyl)-5-bromopyridazine

EXAMPLE 3ai 2-(Perfluoro-1H,1H-nonyloxy)-5-pyridazineboronic acid
Analogously to Example 3aa from 2-(perfluoro-1H,1H-nonyloxy)-5-bromopyridazine

EXAMPLE 3ba

2-Heptyl-5-pyrazineboronic acid
Analogously to Example 3aa from 2-heptyl-5-bromopyrazine

EXAMPLE 3bb

2-Heptyl-5-pyrazineboronic acid
Analogously to Example 3aa from 2-heptyl-5-bromopyrazine

EXAMPLE 3bc 2-(6-Cyclopropylhexoxy)-5-pyrazineboronic acid
Analogously to Example 3aa from 2-(6-cyclopropylhexoxy)-5-bromopyrazine

EXAMPLE 3bd 2-(9-Cyclopropylnonyl)-5-pyrazineboronic acid
Analogously to Example 3aa from 2-(9-cyclopropylnonyl)-5-bromopyrazine

EXAMPLE 3be 2-(3-Oxapentoxy)-5-pyrazineboronic acid
Analogously to Example 3aa from 2-(3-oxapentoxy)-5-bromopyrazine

EXAMPLE 3bf 2-(5-Oxaundecyl)-5-pyrazineboronic acid
Analogously to Example 3aa from 2-(5-oxaundecyl)-5-bromopyrazine

EXAMPLE 3bg 2-(3-Dimethylsilanonyloxy)-5-pyrazineborinic acid
Analogously to Example 3aa from 2-(3-dimethylsilanonyloxy)-5-bromopyrazine

EXAMPLE 3bh 2-(5-Dimethylsiladecyl)-5-pyrazineboronic acid
Analogously to Example 3aa from 2-(5-dimethylsiladecyl)-5-bromopyrazine

EXAMPLE 3bi 2-(Perfluoro-1H,1H-nonyloxy)-5-pyrazineboronic acid
Analogously to Example 3aa from 2-(perfluoro-1H,1H-nonyloxy)-5-bromopyrazine

EXAMPLE 3c

All the compounds obtainable as described in Examples 1 and 2 can be converted into the respective boronic acids analogously to Examples 3a to 3bi.

EXAMPLES 4a–4e

Synthesis of bicyclic substances in which the symbols from formula I have he following meanings:
a,b,m,n,c and d are all zero.

EXAMPLE 4a

3-Octyloxy-6-(6-octyloxypyridin-3-yl)pyridazine
40 ml of toluene are added under a protective gas to 1.41 g (5.8 mmol) of 3-chloro-6-octyloxypyridazine. A solution of 1.45 g (5.8 mmol) of 2-octyloxy-5-pyridineboronic acid in 20 ml of ethanol, followed by 1.23 g of $Na_2CO_3$ and finally 20 ml of water are added. Finally, mg (0.058 mmol) of tetrakis(triphenylphosphine)palladium(0) are added with stirring. The mixture is refluxed for 8 hours and cooled, the phases are separated, the organic phase is washed once with saturated aqueous $NaHCO_3$ solution and dried over $MgSO_4$, and the solvent is removed in vacuo. The residue is chromatographed on $SiO_2$ using $CH_2Cl_2$/ethyl acetate: 20/1. The product obtained can be further purified by recrystallization from n-heptane.
Melting point: X 100 (93) I

EXAMPLE 4b

3-Octyloxy-6-(6-dodecyloxypyridin-3-yl)pyridazine
Analogously to Example 4a from 3-chloro-6-octyloxypyridazine and 2-dodecyloxy-5-pyridineboronic acid
Melting point: X 96 (91) I

EXAMPLE 4c

3-Octyloxy-6-(6-hexoxypyridin-3-yl)pyridazine
Analogously to Example 4a from 3-chloro-6-octyloxypyridazine and 2-hexoxy-5-pyridineboronic acid
Melting point: X 99 (95) $S_b$ 100 (96) I

EXAMPLE 4d 3-(Perfluoro-1H,1H-octyloxy)-6-(6-octyloxypyridin-3-yl)pyridazine

Analogously to Example 4a from 3-chloro-6-(perfluoro-1H,1H-octyloxy)pyridazine and 2-octyloxy-5-pyridineboronic acid Melting point: X 108 (105) I

EXAMPLE 4e

The compounds 4e-1 to 4e-324 can be prepared from the substances described in Examples 1, 2 and 3 analogously to Examples 4a to 4d.

4e-1 3-Octyloxy-6-(6-decyloxypyridin-3-yl)pyridazine
4e-2 3-Octyloxy-6-(6-heptylpyridin-3-yl)pyridazine
4e-3 3-Octyloxy-6-(6-(6-cyclopropylhexoxy)pyridin-3-yl)pyridazine
4e-4 3-Octyloxy-6-(6-(9-cyclopropylnonyl)pyridin-3-yl)pyridazine
4e-5 3-Octyloxy-6-(6-perfluoro-1H,1H-heptyloxypyridin-3-yl)pyridazine
4e-6 3-Octyloxy-6-(6-(5-oxanonyloxy)pyridin-3-yl)pyridazine
4e-7 3-Octyloxy-6-(6-(5-oxaundecyl)pyridin-3-yl)pyridazine
4e-8 3-Octyloxy-6-(6-(6-dimethylsila)decyloxypyridin-3-yl)pyridazine
4e-9 3-Octyloxy-6-(6-(9-dimethylsila)tetradecylpyridin-3-yl)pyridazine
4e-10 3-Heptyl-6-(6-octyloxypyridin-3-yl)pyridazine
4e-11 3-Heptyl-6-(6-heptylpyridin-3-yl)pyridazine
4e-12 3-Heptyl-6-(6-(6-cyclopropylhexoxy)pyridin-3-yl)pyridazine
4e-13 3-Heptyl-6-(6-(9-cyclopropylnonyl)pyridin-3-yl)pyridazine
4e-14 3-Heptyl-6-(6-perfluoro-1H,1H-heptyloxypyridin-3-yl)pyridazine
4e-15 3-Heptyl-6-(6-(5-oxanonyloxy)pyridin-3-yl)pyridazine
4e-16 3-Heptyl-6-(6-(5-oxaundecyl)pyridin-3-yl)pyridazine
4e-17 3-Heptyl-6-(6-(6-dimethylsila)decyloxypyridin-3-yl)pyridazine
4e-18 3-Heptyl-6-(6-(9-dimethylsila)tetradecylpyridin-3-yl)pyridazine
4e-19 3-(6-Cyclopropylhexoxy)-6-(6-octyloxypyridin-3-yl)pyridazine
4e-20 3-(6-Cyclopropylhexoxy)-6-(6-heptylpyridin-3-yl)pyridazine
4e-21 3-(6-Cyclopropylhexoxy)-6-(6-(6-cyclopropylhexoxy)pyridin-3-yl)pyridazine
4e-22 3-(6-Cyclopropylhexoxy)-6-(6-(9-cyclopropylnonyl)pyridin-3-yl)pyridazine
4e-23 3-(6-Cyclopropylhexoxy)-6-(6-perfluoro-1H,1H-heptyloxypyridin-3-yl)pyridazine
4e-24 3-(6-Cyclopropylhexoxy)-6-(6-(5-oxanonyloxy)pyridin-3-yl)pyridazine
4e-25 3-(6-Cyclopropylhexoxy)-6-(6-(5-oxaundecyl)pyridin-3-yl)pyridazine
4e-26 3-(6-Cyclopropylhexoxy)-6-(6-(6-dimethylsila)decyloxypyridin-3-yl)pyridazine
4e-27 3-(6-Cyclopropylhexoxy)-6-(6-(9-dimethylsila)tetradecylpyridin-3-yl)pyridazine
4e-28 3-(9-Cyclopropylnonyl)-6-(6-octyloxypyridin-3-yl)pyridazine
4e-29 3-(9-Cyclopropylnonyl)-6-(6-heptylpyridin-3-yl)pyridazine
4e-30 3-(9-Cyclopropylnonyl)-6-(6-(6-cyclopropylhexoxy)pyridin-3-yl)pyridazine
4e-31 3-(9-Cyclopropylnonyl)-6-(6-(9-cyclopropylnonyl)pyridin-3-yl)pyridazine
4e-32 3-(9-Cyclopropylnonyl)-6-(6-perfluoro-1H,1H-heptyloxypyridin-3-yl)pyridazine
4e-33 3-(9-Cyclopropylnonyl)-6-(6-(5-oxanonyloxy)pyridin-3-yl)pyridazine
4e-34 3-(9-Cyclopropylnonyl)-6-(6-(5-oxaundecyl)pyridin-3-yl)pyridazine
4e-35 3-(9-Cyclopropylnonyl)-6-(6-(6-dimethylsila)decyloxypyridin-3-yl)pyridazine
4e-36 3-(9-Cyclopropylnonyl)-6-(6-(9-dimethylsila)tetradecylpyridin-3-yl)pyridazine
4e-37 3-Perfluoro-1H,1H-heptyloxy-6-(6-octyloxypyridin-3-yl) pyridazine
4e-38 3-Perfluoro-1H,1H-heptyloxy-6-(6-heptylpyridin-3-yl) pyridazine
4e-39 3-Perfluoro-1H,1H-heptyloxy-6-(6-(6-cyclopropylhexoxy)pyridin-3-yl)pyridazine
4e-40 3-Perfluoro-1H,1H-heptyloxy-6-(6-(9-cyclopropylnonyl)pyridin-3-yl) pyridazine
4e-41 3-Perfluoro-1H,1H-heptyloxy-6-(6-perfluoro-1H,1H-heptyloxypyridin-3-yl)pyridazine
4e-42 3-Perfluoro-1H,1H-heptyloxy-6-(6-(5-oxanonyloxy)pyridin-3-yl)pyridazine
4e-43 3-Perfluoro-1H,1H-heptyloxy-6-(6-(5-oxaundecyl)pyridin-3-yl)pyridazine
4e-44 3-Perfluoro-1H,1H-heptyloxy-6-(6-(6-dimethylsila)decyloxypyridin-3-yl)pyridazine
4e-45 3-Perfluoro-1H,1H-heptyloxy-6-(6-(9-dimethylsila)tetradecylpyridin-3-yl)pyridazine
4e-46 3-(5-Oxanonyloxy)-6-(6-octyloxypyridin-3-yl)pyridazine
4e-47 3-(5-Oxanonyloxy)-6-(6-heptylpyridin-3-yl)pyridazine
4e-48 3-(5-Oxanonyloxy)-6-(6-(6-cyclopropylhexoxy)pyridin-3-yl)pyridazine
4e-49 3-(5-Oxanonyloxy)-6-(6-(9-cyclopropylnonyl)pyridin-3-yl)pyridazine
4e-50 3-(5-Oxanonyloxy)-6-(6-perfluoro-1H,1H-heptyloxypyridin-3-yl)pyridazine
4e-51 3-(5-Oxanonyloxy)-6-(6-(5-oxanonyloxy)pyridin-3-yl)pyridazine
4e-52 3-(5-Oxanonyloxy)-6-(6-(5-oxaundecyl)pyridin-3-yl)pyridazine
4e-53 3-(5-Oxanonyloxy)-6-(6-(6-dimethylsila )decyloxypyridin-3-yl)pyridazine
4e-54 3-(5-Oxanonyloxy)-6-(6-(9-dimethylsila )tetradecylpyridin-3-yl)pyridazine
4e-55 3-(5-Oxaundecyl)-6-(6-octyloxypyridin-3-yl)pyridazine
4e-56 3-(5-Oxaundecyl)-6-(6-heptylpyridin-3-yl)pyridazine
4e-57 3-(5-Oxaundecyl)-6-(6-(6-cyclopropylhexoxy)pyridin-3-yl)pyridazine
4e-58 3-(5-Oxaundecyl)-6-(6-(9-cyclopropylnonyl)pyridin-3-yl)pyridazine
4e-59 3-(5-Oxaundecyl)-6-(6-perfluoro-1H,1H-heptyloxypyridin-3-yl)pyridazine
4e-60 3-(5-Oxaundecyl)-6-(6-(5-oxanonyloxy)pyridin-3-yl)pyridazine
4e-61 3-(5-Oxaundecyl)-6-(6-(5-oxaundecyl)pyridin-3-yl)pyridazine
4e-62 3-(5-Oxaundecyl)-6-(6-(6-dimethylsila)decyloxypyridin-3-yl)pyridazine
4e-63 3-(5-Oxaundecyl)-6-(6-(9-dimethylsila)tetradecylpyridin-3-yl)pyridazine 4e-64  3-(6-Dimethylsila)decyloxy-6-(6-octyloxypyridin-3-yl)pyridazine
4e-65  3-(6-Dimethylsila)decyloxy-6-(6-heptylpyridin-3-yl)pyridazine
4e-66  3-(6-Dimethylsila)decyloxy-6-(6-(6-cyclopropylhexoxy)pyridin-3-yl)pyridazine
4e-67  3-(6-Dimethylsila)decyloxy-6-(6-(9-cyclopropyl nonyl)pyridin-3-yl)pyridazine
4e-68  3-(6-Dimethylsila)decyloxy-6-(6-perfluoro-1H,1H-heptyloxypyridin-3-yl)pyridazine
4e-69  3-(6-Dimethylsila)decyloxy-6-(6-(5-oxanonyloxy)pyridin-3-yl)pyridazine
4e-70  3-(6-Dimethylsila)decyloxy-6-(6-(5-oxaundecyl)pyridin-3-yl)pyridazine
4e-71  3-(6-Dimethylsila)decyloxy-6-(6-(6-dimethylsila)decyloxypyridin-3-yl)pyridazine
4e-72  3-(6-Dimethylsila)decyloxy-6-(6-(9-dimethylsila)tetradecylpyridin-3-yl)pyridazine
4e-73  3-(9-Dimethylsila)tetradecyl-6-(6-octyloxypyridin-3-yl)pyridazine
4e-74  3-(9-Dimethylsila)tetradecyl-6-(6-heptylpyridin-3-yl)pyridazine
4e-75  3-(9-Dimethylsila)tetradecyl-6-(6-(6-cyclopropylhexoxy)pyridin- 3-yl)pyridazine
4e-76  3-(9-Dimethylsila)tetradecyl-6-(6-(9-cyclopropylnonyl)pyridin-3-yl)pyridazine
4e-77  3-(9-Dimethylsila)tetradecyl-6-(6-perfluoro-1H,1H-heptyloxypyridin-3-yl)pyridazine
4e-78  3-(9-Dimethylsila)tetradecyl-6-(6-(5-oxanonyloxy)pyridin-3-yl)pyridazine
4e-79  3-(9-Dimethylsila)tetradecyl-6-(6-(5-oxaundecyl)pyridin-3-yl)pyridazine
4e-80  3-(9-Dimethylsila)tetradecyl-6-(6-(6-dimethylsila)decyloxypyridin-3-yl)pyridazine
4e-81  3-(9-Dimethylsila)tetradecyl-6-(6-(9-dimethylsila)tetradecylpyridin-3-yl)pyridazine
4e-82  3-Octyloxy-6-(5-octyloxypyridin-2-yl)pyridazine
4e-83  3-Octyloxy-6-(5-heptylpyridin-2-yl)pyridazine
4e-84  3-Octyloxy-6-(5-(6-cyclopropylhexoxy)pyridin-2-yl)pyridazine
4e-85  3-Octyloxy-6-(5-(9-cyclopropylnonyl)pyridin-2-yl)pyridazine
4e-86  3-Octyloxy-6-(5-perfluoro-1H,1H-heptyloxypyridin-2-yl)pyridazine
4e-87  3-Octyloxy-6-(5-(5-oxanonyloxy)pyridin-2-yl)pyridazine
4e-88  3-Octyloxy-6-(5-(5-oxaundecyl)pyridin-2-yl)pyridazine
4e-89  3-Octyloxy-6-(5-(6-dimethylsila) decyloxypyridin-2-yl)pyridazine
4e-90  3-Octyloxy-6-(5-(9-dimethylsila)tetradecylpyridin-2-yl)pyridazine
4e-91  3-Heptyl-6-(5-octyloxypyridin-2-yl)pyridazine
4e-92  3-Heptyl-6-(5-heptylpyridin-2-yl)pyridazine
4e-93  3-Heptyl-6-(5-(6-cyclopropylhexoxy)pyridin-2-yl)pyridazine
4e-94  3-Heptyl-6-(5-(9-cyclopropylnonyl)pyridin-2-yl)pyridazine
4e-95  3-Heptyl-6-(5-perfluoro-1H,1H-heptyloxypyridin-2-yl)pyridazine
4e-96  3-Heptyl-6-(5-(5-oxanonyloxy)pyridin-2-yl)pyridazine
4e-97  3-Heptyl-6-(5-(5-oxaundecyl)pyridin-2-yl)pyridazine
4e-98  3-Heptyl-6-(5-(6-dimethylsila)decyloxypyridin-2-yl)pyridazine
4e-99  3-Eeptyl-6-(5-(9-dimethylsila)tetradecylpyridin-2-yl)pyridazine
4e-100  3-(6-Cyclopropylhexoxy)-6-(5-octyloxypyridin-2-yl)pyridazine
4e-101  3-(6-Cyclopropylhexoxy)-6-(5-heptylpyridin-2-yl)pyridazine
4e-102  3-(6-Cyclopropylhexoxy)-6-(5-(6-cyclopropylhexoxy)pyridin-2-yl)pyridazine
4e-103  3-(6-Cyclopropylhexoxy)-6-(5-(9-cyclopropylnonyl)pyridin-2-yl)pyridazine
4e-104  3-(6-Cyclopropylhexoxy)-6-(5-perfluoro-1H,1H-heptyloxypyridin-2-yl)pyridazine
4e-105  3-(6-Cyclopropylhexoxy)-6-(5-(5-oxanonyloxy)pyridin-2-yl)pyridazine
4e-106  3-(6-Cyclopropylhexoxy)-6-(5-(5-oxaundecyl)pyridin-2-yl)pyridazine
4e-107  3-(6-Cyclopropylhexoxy)-6-(5-(6-dimethylsila)decyloxypyridin-2-yl)pyridazine
4e-108  3-(6-Cyclopropylhexoxy)-6-(5-(9-dimethylsila)tetradecylpyridin-2-yl)pyridazine
4e-109  3-(9-Cyclopropylnonyl)-6-(5-octyloxypyridin-2-yl)pyridazine
4e-110  3-(9-Cyclopropylnonyl)-6-(5-heptylpyridin-2-yl)pyridazine
4e-111  3-(9-Cyclopropylnonyl)-6-(5-(6-cyclopropylhexoxy)pyridin-2-yl)pyridazine
4e-112  3-(9-Cyclopropylnonyl)-6-(5-(9-cyclopropylnonyl)pyridin-2-yl)pyridazine
4e-113  3-(9-Cyclopropylnonyl)-6-(5-perfluoro-1H,1H-heptyloxypyridin-2-yl)pyridazine
4e-114  3-(9-Cyclopropylnonyl)-6-(5-(5-oxanonyloxy)pyridin-2-yl)pyridazine
4e-115  3-(9-Cyclopropylnonyl)-6-(5-(5-oxaundecyl)pyridin-2-yl)pyridazine
4e-116  3-(9-Cyclopropylnonyl)-6-(5-(6-dimethylsila)decyloxypyridin- 2-yl)pyridazine
4e-117  3-(9-Cyclopropylnonyl)-6-(5-(9-dimethylsila)tetradecylpyridin-2-yl)pyridazine
4e-118  3-perfluoro-1H,1H-heptyloxy-6-(5-octyloxypyridin-2-yl)pyridazine
4e-119  3-perfluoro-1H,1H-heptyloxy-6-(5-heptylpyridin-2-yl)pyridazine
4e-120  3-perfluoro-1H,1H-heptyloxy-6-(5-(6-cyclopropylhexoxy)pyridin-2-yl)pyridazine
4e-121  3-perfluoro-1H,1H-heptyloxy-6-(5-(9-cyclopropylnonyl)pyridin-2-yl)pyridazine
4e-122  3-perfluoro-1H,1H-heptyloxy-6-(5-perfluoro-1H,1H-heptyloxypyridin-2-yl)pyridazine
4e-123  3-perfluoro-1H,1H-heptyloxy-6-(5-(5-oxanonyloxy)pyridin-2-yl)pyridazine
4e-124  3-perfluoro-1H,1H-heptyloxy-6-(5-(5-oxaundecyl)pyridin-2-yl)pyridazine
4e-125  3-perfluoro-1H,1H-heptyloxy-6-(5-(6-dimethylsila)decyloxypyridin-2-yl)pyridazine
4e-126  3-perfluoro-1H,1H-heptyloxy-6-(5-(9-dimethylsila)tetradecylpyridin-2-yl)pyridazine
4e-127  3-(5-Oxanonyloxy)-6-(5-octyloxypyridin-2-yl)pyridazine
4e-128  3-(5-Oxanonyloxy)-6-(5-heptylpyridin-2-yl)pyridazine
4e-129  3-(5-Oxanonyloxy)-6-(5-(6-cyclopropylhexoxy)pyridin-2-yl)pyridazine
4e-130  3-(5-Oxanonyloxy)-6-(5-(9-cyclopropylnonyl)pyridin-2-yl)pyridazine
4e-131  3-(5-Oxanonyloxy)-6-(5-perfluoro-1H,1H-heptyloxypyridin-2-yl)pyridazine
4e-132  3-(5-Oxanonyloxy)-6-(5-(5-oxanonyloxy)pyridin-2-yl)pyridazine
4e-133  3-(5-Oxanonyloxy)-6-(5-(5-oxaundecyl)pyridin-2-yl)pyridazine 4e-134 3-(5-Oxanonyloxy)-6-(5-(6-dimethylsila)decyloxypyridin-2-yl)pyridazine
4e-135 3-(5-Oxanonyloxy)-6-(5-(9-dimethylsila)tetradecylpyridin-2-yl)pyridazine
4e-136 3-(5-Oxaundecyl)-6-(5-octyloxypyridin-2-tl)pyridazine
4e-137 3-(5-Oxaundecyl)-6-(5-heptylpyridin-2-yl)pyridazine
4e-138 3-(5-Oxaundecyl)-6-(5-(6-cyclopropylhexoxY)pyridin-2-yl)pyridazine
4e-139 3-(5-Oxaundecyl)-6-(5-(9-cyclopropylnonyl)pyridin-2-yl)pyridazine
4e-140 3-(5-Oxaundecyl)-6-(5-perfluoro-1H,1H-heptyloxypyridin-2-yl)pyridazine
4e-141 3-(5-Oxaundecyl)-6-(5-(5-oxanonyloxy)pyridin-2-yl)pyridazine
4e-142 3-(5-Oxaundecyl)-6-(5-(5-oxaundecyl)pyridin-2-yl)pyridazine
4e-143 3-(5-Oxaundecyl)-6-(5-(6-dimethylsila)decyloxypyridin-2-yl)pyridazine
4e-144 3-(5-Oxaundecyl)-6-(5-(9-dimethylsila)tetradecylpyridin-2-yl)pyridazine
4e-145 3-(6-Dimethylsila)decyloxy-6-(5-octyloxypyridin-2-yl)pyridazine
4e-146 3-(6-Dimethylsila)decyloxy-6-(5-heptylpyridin-2-yl)pyridazine
4e-147 3-(6-Dimethylsila)decyloxy-6-(5-(6-cyclopropylhexoxy)pyridin-2-yl)pyridazine
4e-148 3-(6-Dimethylsila)decyloxy-6-(5-(9-cyclopropylnonyl)pyridin-2-yl)pyridazine
4e-149 3-(6-Dimethylsila)decyloxy-6-(5-perfluoro-1H,1H-heptyloxypyridin-2-yl)pyridazine
4e-150 3-(6-Dimethylsila)decyloxy-6-(5-(5-oxanonyloxy)pyridin-2-yl)pyridazine
4e-151 3-(6-Dimethylsila)decyloxy-6-(5-(5-oxaundecyl)pyridin-2-yl)pyridazine
4e-152 3-(6-Dimethylsila)decyloxy-6-(5-(6-dimethylsila)decyloxypyridin-2-yl)pyridazine
4e-153 3-(6-Dimethylsila)decyloxy-6-(5-(9-dimethylsila)tetradecylpyridin-2-yl)pyridazine
4e-154 3-(9-Dimethylsila)tetradecyl-6-(5-octyloxypyridin-2-yl)pyridazine
4e-155 3-(9-Dimethylsila)tetradecyl-6-(5-heptylpyridin-2-yl)pyridazine
4e-156 3-(9-Dimethylsila)tetradecyl-6-(5-(6-cyclopropylhexoxy)pyridin-2-yl)pyridazine
4e-157 3-(9-Dimethylsila)tetradecyl-6-(5-(9-cyclopropylnonyl)pyridin-2-yl)pyridazine
4e-158 3-(9-Dimethylsila)tetradecyl-6-(5-perfluoro-1H,1H-heptyloxypyridin-2-yl)pyridazine
4e-159 3-(9-Dimethylsila)tetradeoyl-6-(5-(5-oxanonyloxy)pyridin-2-yl)pyridazine
4e-160 3-(9-Dimethylsila)tetradecyl-6-(5-(5-oxaundecyl)pyridin-2-yl)pyridazine
4e-161 3-(9-Dimethylsila)tetradeoyl-6-(5-(6-dimethylsila)decyloxypyridin-2-yl)pyridazine
4e-162 3-(9-Dimethylsila)tetradeoyl-6-(5-(9-dimethylsila)tetradecylpyridin-2-yl)pyridazine
4e-163 3-Octyloxy-6-(6-octyloxypyridin-3-yl)pyrazine
4e-164 3-Octyloxy-6-(6-heptylpyridin-3-yl)pyrazine
4e-165 3-Octyloxy-6-(6-(6-cyclopropylhexoxy)pyridin-3-yl)pyrazine
4e-166 3-Octyloxy-6-(6-(9-cyclopropylnonyl)pyridin-3-yl)pyrazine
4e-167 3-Octyloxy-6-(6-perfluoro-1H,1H-heptyloxypyridin-3-yl)pyrazine
4e-168 3-Octyloxy-6-(6-(5-oxanonyloxy)pyridin-3-yl)pyrazine
4e-169 3-Octyloxy-6-(6-(5-oxaundecyl)pyridin-3-yl)pyrazine
4e-170 3-Octyloxy-6-(6-(6-dimethylsila)deoyloxypyridin-3-yl)pyrazine
4e-171 3-Octyloxy-6-(6-(9-dimethylsila)tetradecylpyridin-3-yl)pyrazine
4e-172 3-Heptyl-6-(6-octyloxypyridin-3-yl)pyrazine
4e-173 3-Heptyl-6-(6-heptylpyridin-3-yl)pyrazine
4e-174 3-Heptyl-6-(6-(6-cyolopropylhexoxy)pyridin-3-yl)pyrazine
4e-175 3-Heptyl-6-(6-(9-cyclopropylnonyl)pyridin-3-yl)pyrazine
4e-176 3-Heptyl-6-(6-perfluoro-1H,1H-heptyloxypyridin-3-yl)pyrazine
4e-177 3-Heptyl-6-(6-(5-oxanonyloxy)pyridin-3-yl)pyrazine
4e-178 3-Heptyl-6-(6-(5-oxaundecyl)pyridin-3-yl)pyrazine
4e-179 3-Heptyl-6-(6-(6-dimethylsila)decyloxypyridin-3-yl)pyrazine
4e-180 3-Heptyl-6-(6-(9-dimethylsila)tetradecylpyridin-3-yl)pyrazine
4e-181 3-(6-Cyclopropylhexoxy)-6-(6-octyloxypyridin-3-yl)pyrazine
4e-182 3-(6-Cyclopropylhexoxy)-6-(6-heptylpyridin-3-yl)pyrazine 4
4e-183 3-(6-Cyclopropylhexoxy)-6-(6-(6-cyclopropylhexoxy)pyridin-3-yl)pyrazine
4e-184 3-(6-Cyclopropylhexoxy)-6-(6-(9-cyclopropylnonyl)pyridin-3-yl)pyrazine
4e-185 3-(6-Cyclopropylhexoxy)-6-(6-perfluoro-1H,1H-heptyloxypyridin-3-yl)pyrazine
4e-186 3-(6-Cyclopropylhexoxy)-6-(6-(5-oxanonyloxy)pyridin-3-yl)pyrazine
4e-187 3-(6-Cyclopropylhexoxy)-6-(6-(5-oxaundecyl)pyridin-3-yl)pyrazine
4e-188 3-(6-Cyclopropylhexoxy)-6-(6-(6-dimethylsila)decyloxypyridin-3-yl)pyrazine
4e-189 3-(6-Cyclopropylhexoxy)-6-(6-(9-dimethylsila)tetradecylpyridin-3-yl)pyrazine
4e-190 3-(9-Cyclopropylnonyl)-6-(6-octyloxypyridin-3-yl)pyrazine
4e-191 3-(9-Cyclopropylnonyl)-6-(6-heptylpyridin-3-yl)pyrazine
4e-192 3-(9-Cyclopropylnonyl)-6-(6-(6-cyclopropylhexoxy)pyridin-3-yl)pyrazine
4e-193 3-(9-Cyclopropylnonyl)-6-(6-(9-cyclopropylnonyl)pyridin-3-yl)pyrazine
4e-194 3-(9-Cyclopropylnonyl)-6-(6-perfluoro-1H,1H-heptyloxypyridin-3-yl)pyrazine
4e-195 3-(9-Cyclopropylnonyl)-6-(6-(5-oxanonyloxy)pyridin-3-yl)pyrazine
4e-196 3-(9-Cyclopropylnonyl)-6-(6-(5-oxaundecyl)pyridin- 3-yl)pyrazine
4e-197 3-(9-Cyclopropylnonyl)-6-(6-(6-dimethylsila)decyloxypyridin-3-yl)pyrazine
4e-198 3-(9-Cyclopropylnonyl)-6-(6-(9-dimethylsila)tetradecylpyridin-3-yl)pyrazine
4e-199 3-perfluoro-1H,1H-heptyloxy-6-(6-octyloxypyrdin-3-yl)pyrazine
4e-200 3-perfluoro-1H,1H-heptyloxy-6-(6-heptylpyridin-3-yl)pyrazine
4e-201 3-perfluoro-1H,1H-heptyloxy-6-(6-(6-cyclopropylhexoxy)pyridin-3-yl)pyrazine
4e-202 3-perfluoro-1H,1H-heptyloxy-6-(6-(9-cyclopropylnonyl)pyridin-3-yl)pyrazine
4e-203 3-perfluoro-1H,1H-heptyloxy-6-(6-perfluoro-1H,1H-heptyloxypyridin-3-yl)pyrazine 4e-204 3-perfluoro-1H,1H-heptyloxy-6-(6-(5-oxanonyloxy)pyridin-3-yl)pyrazine
4e-205 3-perfluoro-1H,1H-heptyloxy-6-(6-(5-oxaundecyl)pyridin-3-yl)pyrazine
4e-206 3-perfluoro-1H,1H-heptyloxy-6-(6-(6-dimethylsila)decyloxypyridin-3-yl)pyrazine
4e-207 3-perfluoro-1H,1H-heptyloxy-6-(6-(9-dimethylsila)tetradecylpyridin-3-yl)pyrazine
4e-208 3-(5-Oxanonyloxy)-6-(6-octyloxypyridin-3-yl)pyrazine
4e-209 3-(5-Oxanonyloxy)-6-(6-heptylpyridin-3-yl)pyrazine
4e-210 3-(5-Oxanonyloxy)-6-(6-(6-cyclopropylhexoxy)pyridin-3-yl)pyrazine
4e-211 3-(5-Oxanonyloxy)-6-(6-(9-cyclopropylnonyl)pyridin-3-yl)pyrazine
4e-212 3-(5-Oxanonyloxy)-6-(6-(6-perfluoro-1H,1H-heptyloxypyridin-3-yl)pyrazine
4e-213 3-(5-Oxanonyloxy)-6-(6-(5-oxanonyloxy)pyridin-3-yl)pyrazine
4e-214 3-(5-Oxanonyloxy)-6-(6-(5-oxaundecyl)pyridin-3-yl)pyrazine
4e-215 3-(5-Oxanonyloxy)-6-(6-(6-dimethylsila)decyloxypyridin-3-yl)pyrazine
4e-216 3-(5-Oxanonyloxy)-6-(6-(9-dimethylsila)tetradecyl)pyridin-3-yl)pyrazine
4e-217 3-(5-Oxaundecyl)-6-(6-octyloxypyridin-3-yl)pyrazine
4e-218 3-(5-Oxaundecyl)-6-(6-heptylpyridin-3-yl)pyrazine
4e-219 3-(5-Oxaundecyl)-6-(6-(6-cyclopropylhexoxy)pyridin-3-yl)pyrazine
4e-220 3-(5-Oxaundecyl)-6-(6-(9-cyclopropylnonyl)pyridin-3-yl)pyrazine
4e-221 3-(5-Oxaundecyl)-6-(6-perfluoro-1H,1H-heptyloxypyridin-3-yl)pyrazine
4e-222 3-(5-Oxaundecyl)-6-(6-(5-oxanonyloxy)pyridin-3-yl)pyrazine
4e-223 3-(5-Oxaundecyl)-6-(6-(5-oxaundecyl)pyridin-3-yl)pyrazine
4e-224 3-(5-Oxaundecyl)-6-(6-(6-dimethylsila)decyloxypyridin-3-yl)pyrazine
4e-225 3-(5-Oxaundecyl)-6-(6-(9-dimethylsila)tetradecylpyridin-3-yl)pyrazine
4e-226 3-(6-Dimethylsila)decyloxy-6-(6-octyloxypyridin-3-yl)pyrazine
4e-227 3-(6-Dimethylsila)decyloxy-6-(6-heptylpyridin-3-yl)pyrazine
4e-228 3-(6-Dimethylsila)decyloxy-6-(6-(6-cyclopropylhexoxy)pyridin-3-yl)pyrazine
4e-229 3-(6-Dimethylsila)decyloxy-6-(6-(9-cyclopropylnonyl)pyridin-3-yl)pyrazine
4e-230 3-(6-Dimethylsila)decyloxy-6-(6-perfluoro-1H,1H-heptyloxypyridin-3-yl)pyrazine
4e-231 3-(6-Dimethylsila)decyloxy-6-(6-(5-oxanonyloxy)pyridin-3-yl)pyrazine
4e-232 3-(6-Dimethylsila)decyloxy-6-(6-(5-oxaundecyl)pyridin-3-yl)pyrazine
4e-233 3-(6-Dimethylsila)decyloxy-6-(6-(6-dimethylsila)decyloxypyridin-3-yl)pyrazine
4e-234 3-(6-Dimethylsila)decyloxy-6-(6-(9-dimethylsila)tetradecylpyridin-3-yl)pyrazine
4e-235 3-(9-Dimethylsila)tetradecyl-6-(6-octyloxypyridin-3-yl)pyrazine
4e-236 3-(9-Dimethylsila)tetradecyl-6-(6-heptylpyridin-3-yl)pyrazine
4e-237 3-(9-Dimethylsila)tetradecyl-6-(6-(6-cyclopropylhexoxy)pyridin-3-yl)pyrazine
4e-238 3-(9-Dimethylsila)tetradecyl-6-(6-(9-cyclopropylnonyl)pyridin-3-yl)pyrazine
4e-239 3-(9-Dimethylsila)tetradecyl-6-(6-perfluoro-1H,1H-heptyloxypyridin-3-yl)pyrazine
4e-240 3-(9-Dimethylsila)tetradecyl-6-(6-(5-oxanonyloxy)pyridin-3-yl)pyrazine
4e-241 3-(9-Dimethylsila)tetradecyl-6-(6-(5-oxaundecyl)pyridin-3-yl)pyrazine
4e-242 3-(9-Dimethylsila)tetradecyl-6-(6-(6-dimethylsila)decyloxypyridin-3-yl)pyrazine
4e-243 3-(9-Dimethylsila)tetradecyl-6-(6-(9-dimethylsila)tetradecylpyridin-3-yl)pyrazine
4e-244 3-Octyloxy-6-(5-octyloxypyridin-2-yl)pyrazine
4e-245 3-Octyloxy-6-(5-heptylpyridin-2-yl)pyrazine
4e-246 3-Octyloxy-6-(5-(6-cyclopropylhexoxy)pyridin-2-yl)pyrazine
4e-247 3-Octyloxy-6-(5-(9-cyclopropylnonyl)pyridin-2-yl)pyrazine
4e-248 3-Octyloxy-6-(5-perfluoro-1H,1H-heptyloxypyridin-2-yl)pyrazine
4e-249 3-Octyloxy-6-(5-(5-oxanonyloxy)pyridin-2-yl)pyrazine
4e-250 3-Octyloxy-6-(5-(5-oxaundecyl)pyridin-2-yl)pyrazine
4e-251 3-Octyloxy-6-(5-(6-dimethylsila)decyloxypyridin-2-yl)pyrazine
4e-252 3-Octyloxy-6-(5-(9-dimethylsila)tetradecylpyridin-2-yl)pyrazine
4e-253 3-Heptyl-6-(5-octyloxypyridin-2-yl)pyrazine
4e-254 3-Heptyl-6-(5-heptylpyridin-2-yl)pyrazine
4e-255 3-Heptyl-6-(5-(6-cyclopropylhexoxy)pyridin-2-yl)pyrazine
4e-256 3-Heptyl-6-(5-(9-cyclopropylnonyl)pyridin-2-yl)pyrazine
4e-257 3-Heptyl-6-(5-perfluoro-1H,1H-heptyloxypyridin-2-yl)pyrazine
4e-258 3-Heptyl-6-(5-(5-oxanonyloxy)pyridin-2-yl)pyrazine
4e-259 3-Heptyl-6-(5-(5-oxaundecyl)pyridin-2-yl)pyrazine
4e-260 3-Heptyl-6-(5-(6-dimethylsila)decyloxypyridin-2-yl)pyrazine
4e-261 3-Heptyl-6-(5-(9-dimethylsila)tetradecylpyridin-2-yl)pyrazine
4e-262 3-(6-Cyclopropylhexoxy)-6-(5-octyloxypyridin-2-yl)pyrazine
4e-263 3-(6-Cyclopropylhexoxy)-6-(5-heptylpyridin-2-yl)pyrazine
4e-264 3-(6-Cyclopropylhexoxy)-6-(5-(6-cyclopropylhexoxy)pyridin-2-yl)pyrazine
4e-265 3-(6-Cyclopropylhexoxy)-6-(5-(9-cyclopropylnonyl)pyridin-2-yl)pyrazine
4e-266 3-(6-Cyclopropylhexoxy)-6-(5-perfluoro-1H,1H-heptyloxypyridin-2-yl)pyrazine
4e-267 3-(6-Cyclopropylhexoxy)-6-(5-(5-oxanonyloxy)pyridin-2-yl)pyrazine
4e-268 3-(6-Cyclopropylhexoxy)-6-(5-(5-oxaundecyl)pyridin-2-yl)pyrazine
4e-269 3-(6-Cyclopropylhexoxy)-6-(5-(6-dimethylsila)decyloxypyridin-2-yl)pyrazine
4e-270 3-(6-Cyclopropylhexoxy)-6-(5-(9-dimethylsila)tetradecylpyridin-2-yl)pyrazine
4e-271 3-(9-Cyclopropylnonyl)-6-(5-octyloxypyridin-2-yl)pyrazine
4e-272 3-(9-Cyclopropylnonyl)-6-(5-heptylpyridin-2-yl)pyrazine
4e-273 3-(9-Cyclopropylnonyl)-6-(5-(6-cyclopropylhexoxy)pyridin-2-yl)pyrazine 4e-274 3-(9-Cyclopropylnonyl)-6-(5-(9-cyclopropylnonyl)pyridin-2-yl)pyrazine
4e-275 3-(9-Cyclopropylnonyl)-6-(5-perfluoro-1H,1H-heptyloxypyridin-2-yl)pyrazine
4e-276 3-(9-Cyclopropylnonyl)-6-(5-(5-oxanonyloxy)pyridin-2-yl)pyrazine
4e-277 3-(9-Cyclopropylnonyl)-6-(5-(5-oxaundecyl)pyridin-2-yl)pyrazine
4e-278 3-(9-Cyclopropylnonyl)-6-(5-(6-dimethylsila)decyloxypyridin-2-yl)pyrazine
4e-279 3-(9-Cyclopropylnonyl)-6-(5-(9-dimethylsila)tetradecylpyridin-2-yl)pyrazine
4e-280 3-Perfluoro-1H,1H-heptyloxy-6-(5-octyloxypyridin-2-yl)pyrazine
4e-281 3-Perfluoro-1H,1H-heptyloxy-6-(5-heptylpyridin-2-yl)pyrazine
4e-282 3-Perfluoro-1H,1H-heptyloxy-6-(5-(6-cyclopropylhexoxy)pyridin-2-yl)pyrazine
4e-283 3-Perfluoro-1H,1H-heptyloxy-6-(5-(9-cyclopropylnonyl)pyridin-2-yl)pyrazine
4e-284 3-Perfluoro-1H,1H-heptyloxy-6-(5-perfluoro-1H,1H-heptyloxypyridin-2-yl)pyrazine
4e-285 3-Perfluoro-1H,1H-heptyloxy-6-(5-(5-oxanonyloxy)pyridin-2-yl)pyrazine
4e-286 3-Perfluoro-1H,1H-heptyloxy-6-(5-(5-oxaundecyl)pyridin-2-yl)pyrazine
4e-287 3-Perfluoro-1H,1H-heptyloxy-6-(5-(6-dimethylsila)decyloxypyridin-2-yl)pyrazine
4e-288 3-Perfluoro-1H,1H-heptyloxy-6-(5-(9-dimethylsila)tetradecylpyridin-2-yl)pyrazine
4e-289 3-(5-Oxanonyloxy)-6-(5-octyloxypyridin-2-yl)pyrazine
4e-290 3-(5-Oxanonyloxy)-6-(5-heptylpyridin-2-yl)pyrazine
4e-291 3-(5-Oxanonyloxy)-6-(5-(6-cyclopropylhexoxy)pyridin-2-yl)pyrazine
4e-292 3-(5-Oxanonyloxy)-6-(5-(9-cyclopropylnonyl)pyridin-2-yl)pyrazine
4e-293 3-(5-Oxanonyloxy)-6-(5-perfluoro-1H,1H-heptyloxypyridin-2-yl)pyrazine
4e-294 3-(5-Oxanonyloxy)-6-(5-(5-oxanonyloxy)pyridin-2-yl)pyrazine
4e-295 3-(5-Oxanonyloxy)-6-(5-(5-oxaundecyl)pyridin-2-yl)pyrazine
4e-296 3-(5-Oxanonyloxy)-6-(5-(6-dimethylsila)decyloxypyridin-2-yl)pyrazine
4e-297 3-(5-Oxanonyloxy)-6-(5-(9-dimethylsila)tetradecylpyridin-2-yl)pyrazine
4e-298 3-(5-Oxaundecyl)-6-(5-octyloxypyridin-2-yl)pyrazine
4e-299 3-(5-Oxaundecyl)-6-(5-heptylpyridin-2-yl)pyrazine
4e-300 3-(5-Oxaundecyl)-6-(5-(6-cyclopropylhexoxy)pyridin-2-yl)pyrazine
4e-301 3-(5-Oxaundecyl)-6-(5-(9-cyclopropylnonyl)pyridin-2-yl)pyrazine
4e-302 3-(5-Oxaundecyl)-6-(5-perfluoro-1H,1H-heptyloxypyridin-2-yl)pyrazine
4e-303 3-(5-Oxaundecyl)-6-(5-(5-oxanonyloxy)pyridin-2-yl)pyrazine
4e-304 3-(5-Oxaundecyl)-6-(5-(5-oxaundecyl)pyridin-2-yl)pyrazine
4e-305 3-(5-Oxaundecyl)-6-(5-(6-dimethylsila)decyloxypyridin-2-yl)pyrazine
4e-306 3-(5-Oxaundecyl)-6-(5-(9-dimethylsila)tetradecylpyridin-2-yl)pyrazine
4e-307 3-(6-Dimethylsila)decyloxy-6-(5-octyloxypyridin-2-yl)pyrazine
4e-308 3-(6-Dimethylsila)decyloxy-6-(5-heptylpyridin-2-yl)pyrazine
4e-309 3-(6-Dimethylsila)decyloxy-6-(5-(6-cyclopropylhexoxy)pyridin-2-yl)pyrazine
4e-310 3-(6-Dimethylsila)decyloxy-6-(5-(9-cyclopropylnonyl)pyridin-2-yl)pyrazine
4e-311 3-(6-Dimethylsila)decyloxy-6-(5-perfluoro-1H,1H-heptyloxypyridin-2-yl)pyrazine
4e-312 3-(6-Dimethylsila)decyloxy-6-(5-(5-oxanonyloxy)pyridin-2-yl)pyrazine
4e-313 3-(6-Dimethylsila)decyloxy-6-(5-(5-oxaundecyl)pyridin-2-yl)pyrazine
4e-314 3-(6-Dimethylsila)decyloxy-6-(5-(6-dimethylsila)decyloxypyridin-2-yl)pyrazine
4e-315 3-(6-Dimethylsila)decyloxy-6-(5-(9-dimethylsila)tetradecylpyridin-2-yl)pyrazine
4e-316 3-(9-Dimethylsila)tetradecyl-6-(5-octyloxypyridin-2-yl)pyrazine
4e-317 3-(9-Dimethylsila)tetradecyl-6-(5-heptylpyridin-2-yl)pyrazine
4e-318 3-(9-Dimethylsila)tetradecyl-6-(5-(6-cyclopropylhexoxy)pyridin-2-yl)pyrazine
4e-319 3-(9-Dimethylsila)tetradecyl-6-(5-(9-cyclopropylnonyl)pyridin-2-yl)pyrazine
4e-320 3-(9-Dimethylsila)tetradecyl-6-(5-perfluoro-1H,1H-heptyloxypyridin-2-yl)pyrazine
4e-321 3-(9-Dimethylsila)tetradecyl-6-(5-(5-oxanonyloxy)pyridin-2-yl)pyrazine
4e-322 3-(9-Dimethylsila)tetradecyl-6-(5-(5-oxaundecyl)pyridin-2-yl)pyrazine
4e-323 3-(9-Dimethylsila)tetradecyl-6-(5-(6-dimethylsila)decyloxypyridin-2-yl)pyrazine
4e-324 3-(9-Dimethylsila)tetradecyl-6-(5-(9-dimethylsila)tetradecylpyridin-2-yl)pyrazine EXAMPLES 5a–c: Preparation of tricyclic substances containing identical wing groups $R^1$ and $R^2$ in accordance with scheme E EXAMPLE 5a 3,6-Bis(2-decyloxypyridin-5-yl)pyridazine

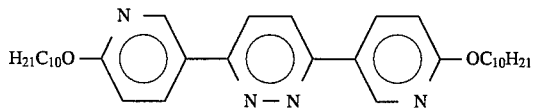

1.6 g (5.73 mmol) of 2-decyloxypyridin-5-boronic acid, 0.28 g (1.91 mmol) of 3,6-dichloropyridazine, 0.03 g (0.024 mmol) of tetrakis(triphenylphosphine)palladium(0) and 0.97 g (9.17 mmol) of sodium carbonate are heated at 80° C. for 24 hours in 30 ml of toluene, 20 ml of ethanol and 10 ml of water. The palladium catalyst is subsequently separated from the reaction mixture by filtration at 80° C. The aqueous lower phase of the reaction mixture is separated off at 80° C., and the organic phase is then freed from solvents in a rotary evaporator and dried in a high vacuum. The crude product obtained in this way is chromatographed on silica gel using dichloromethane/ethyl acetate=20/1 and subsequently recrystallized from acetonitrile, giving 0.38 g of 3,6-bis(2-decyloxypyridin-5-yl)pyridazine (99.5% according to HPLC).

The compound has the following phase sequence: X 127 $S_1$ 125 I

EXAMPLE 5b 3,6-Bis(2-hexoxypyridin-5-yl)pyridazine

Analogously to Example 5a from 2-decyloxypyridin-5-boronic acid and 3,6-dichloropyridazine.

The compound has the following phase sequence:

X 150(138) $S_3$ 164 $S_C$ 209 $S_A$ 235 I

EXAMPLE 5c

The compounds 5c-1 to 5c-42 can be prepared from the substances described in Examples 1, 2 and 3 analogously to Examples 5a and 5b.

5c-1 3,6-Bis(2-octyloxypyridin-5-yl)pyridazine
5c-2 3,6-Bis(2-heptylpyridin-5-yl)pyridazine
5c-3 3,6-Bis(2-(6-cyclopropylhexoxy)pyridin-5-yl)pyridazine
5c-4 3,6-Bis(2-(9-cyclopropylnonyl)pyridin-5-yl)pyridazine
5c-5 3,6-Bis(2-perfluoro-1H,1H-heptyloxypyridin-5-yl)pyridazine
5c-6 3,6-Bis(2-(5-oxanonyloxy)pyridin-5-yl)pyridazine
5c-7 3,6-Bis(2-(5-oxaundecyl)pyridin-5-yl)pyridazine
5c-8 3,6-Bis(2-(6-dimethylsila)decyloxypyridin-5-yl)pyridazine
5c-9 3,6-Bis(2-(9-dimethylsila)tetradecylpyridin-5-yl)pyridazine
5c-10 2,5-Bis(2-octyloxypyridin-5-yl)pyrazine
5c-11 2,5-Bis(2-heptylpyridin-5-yl)pyrazine
5c-12 2,5-Bis(2-(6-cyclopropylhexoxy)pyridin-5-yl)pyrazine
5c-13 2,5-Bis(2-(9-cyclopropylnonyl)pyridin-5-yl)pyrazine
5c-14 2,5-Bis(2-perfluoro-1H,1H-heptyloxypyridin-5-yl)pyrazine
5c-15 2,5-Bis(2-(5-oxanonyloxy)pyridin-5-yl)pyrazine
5c-16 2,5-Bis(2-(5-oxaundecyl)pyridin-5-yl)pyrazine
5c-17 2,5-Bis(2-(6-dimethylsila)decyloxypyridin-5-yl)pyrazine
5c-18 2,5-Bis(2-(9-dimethylsila)tetradecylpyridin-5-yl)pyrazine
5c-19 3,6-Bis(5-octyloxypyridin-2-yl)pyridazine
5c-20 3,6-Bis(5-heptylpyridin-2-yl)pyridazine
5c-21 3,6-Bis(5-(6-cyclopropylhexoxy)pyridin-2-yl)pyridazine
5c-22 3,6-Bis(5-(9-cyclopropylnonyl)pyridin-2-yl)pyridazine
5c-23 3,6-Bis(5-perfluoro-1H,1H-heptyloxypyridin-2-yl)pyridazine
5c-24 3,6-Bis(5-(5-oxanonyloxy)pyridin-2-yl)pyridazine
5c-25 3,6-Bis(5-(5-oxaundecyl)pyridin-2-yl)pyridazine
5c-26 3,6-Bis(5-(6-dimethylsila)decyloxypyridin-2-yl)pyridazine
5c-27 3,6-Bis(5-(9-dimethylsila)tetradecylpyridin-2-yl)pyridazine
5c-28 2,5-Bis(5-octyloxypyridin-2-yl)pyrazine
5c-29 2,5-Bis(5-heptylpyridin-2-yl)pyrazine
5c-30 2,5-Bis(5-(6-cyclopropylhexoxy)pyridin-2-yl)pyrazine
5c-31 2,5-Bis(5-(9-cyclopropylnonyl)pyridin-2-yl)pyrazine
5c-32 2,5-Bis(5-perfluoro-1H,1H-heptyloxypyridin-2-yl)pyrazine
5c-33 2,5-Bis(5-(5-oxanonyloxy)pyridin-2-yl)pyrazine
5c-34 2,5-Bis(5-(5-oxaundecyl)pyridin-2-yl)pyrazine
5c-35 2,5-Bis(5-(6-dimethylsila)decyloxypyridin-2-yl)pyrazine
5c-36 2,5-Bis(5-(9-dimethylsila)tetradecylpyridin-2-yl)pyrazine
5c-37 2,5-Bis(2-octyloxypyrazin-5-yl)pyridine
5c-38 2,5-Bis(3-octyloxypyridazin-6-yl)pyridine
5c-39 2,5-Bis(2-octylpyrazin-5-yl)pyridine
5c-40 2,5-Bis(3-octylpyridazin-6-yl)pyridine
5c-41 3,6-Bis(2-octylpyrazin-5-yl)pyridazine
5c-42 2,5-Bis(3-octylpyridazin-6-yl)pyrazine

EXAMPLE 6

Preparation of tricyclic substances in which one of the rings contains no nitrogen.

EXAMPLE 6aa

3-[6-(4-Benzyloxyphenyl)pyridin-3-yl ]-6-octyloxypyridazine

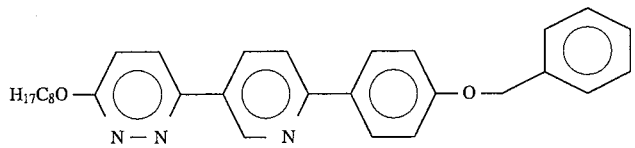

Step 1

In accordance with scheme C-I, 10 g of 2,5-dibromopyridine and 19.24 g of 4-benzyloxyphenylboronic acid are coupled analogously to Example 4a to give 21.2 g (73.9%) of 5-bromo-2-(4-benzyloxyphenyl)pyridine.

Step 2

In accordance with scheme C-III, 20 g (29.4 mmol) of 5-bromo-2-(4-benzyloxyphenyl)pyridine are converted analogously to Example 3a into 2-(4-benzyloxyphenyl)pyridin-5-boronic acid.

Step 3

In accordance with scheme D, 11.82 g (38.75 mmol) of 2-(4-benzyloxyphenyl)pyridin-5-boronic acid are reacted with 7.52 g (31 mmol) of 3-chloro-6-octyloxypyridazine analogously to Example 4a to give 6.02 g (42%) of 3-[6-(4-benzyloxyphenyl)pyridin-3-yl]-6-octyloxypyridazine.

EXAMPLE 6ab

4-[5-(6-Octyloxypyridazin-3-yl)pyridin-2-yl]phenol

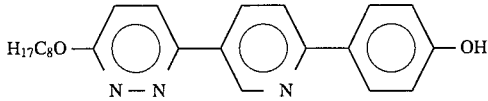

6.02 g (12.9 mmol) of 3-[6-(4-benzyloxyphenyl)pyridin-3-yl]-6-octyloxypyridazine are dissolved in 700 ml of absolute THF at 50° C., 3.0 g of palladium on charcoal are added, and the mixture is hydrogenated at 50° C. After filtration, the filtrate is evaporated in a rotary evaporator. The residue is chromatographed on $SiO_2$ using $CH_2Cl_2$/ethyl acetate, giving 2.0 g of 4-[5-(6-octyloxypyridazin-3-yl)pyridin-2-yl] phenol.

EXAMPLE 6ac

3-Octyloxy-6-[6-(4-octyloxyphenyl)pyridin-3-yl ]pyridazine

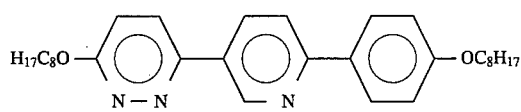

0.6 g (1.6 mmol) of 4-[5-(6-octyloxypyridazin-3-yl)pyridin-2-yl]phenol is dissolved in 20 ml of DMF, 0.1 g of NaH (60% in mineral oil) is added at room temperature, the mixture is stirred for 30 minutes, and 0.46 g (2.4 mmol) of 1-bromooctane is then added. The mixture is stirred for a further 20 hours and poured into 200 ml of $H_2O$, and the precipitate is filtered off with suction. Purification is carried out by chromatography on $SiO_2$ using $CH_2Cl_2$/ethyl acetate: 95/5, giving 0.43 g of 3-octyloxy-6-[6-(4-octyloxyphenyl)pyridin-3-yl]pyridazine.
Phases: X 107 (85) $S_C$ 222 I

EXAMPLE 6ad

3-Octyloxy-6-[6-(4-{6-cyclopropylhexoxy}phenyl)pyridin-3-yl ]pyridazine

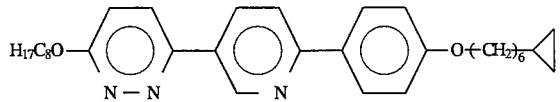

Analogously to Example 6ac from 4-[5-(6-octyloxypyridazin-3-yl)pyridin-2-yl ]phenol and 6-cyclopropylhexyl bromide.

EXAMPLE 6ae

3-Octyloxy-6-[6-(4-{5-oxanonyloxy}phenyl)pyridin-3-yl ]pyridazine

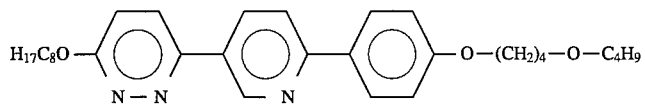

Analogously to Example 6ac from 4-[5-(6-octyloxypyridazin-3-yl)pyridin-2-yl]phenol and 5-oxanonyl bromide.

EXAMPLE 6af

3-Octyloxy-6-[6-(4-{5-(dimethylsila)nonyloxy}phenyl)pyridin-3-yl ]pyridazine

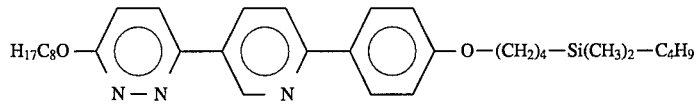

Analogously to Example 6ac from 4-[5-(6-octyloxypyridazin-3-yl)pyridin-2-yl ]phenol and 5-(dimethylsila)nonyl bromide.

EXAMPLE 6ag

3-Octyloxy-6-[6-(4-{(2S,3S)-3-butyl-oxiran-2-ylmethoxy}phenyl)pyridin-3-yl ]pyridazine

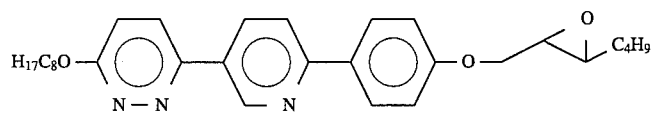

By etherification by the method of Mitsunobu (for example O. Mitsunobu, Synthesis 1981, 1) of 4-[5-(6-octyloxypyridazin-3-yl)pyridin-2-yl]phenol using (2S,3S)-2-hydroxymethyl-3-butyloxirane.
Phases X 128 (106) $S_C$ * 233 I

EXAMPLE 6ah

3-Octyloxy-6-[6-(4-{(4S)-2,2-dimethyl[1,3]-dioxolan-4-ylmethoxy}phenyl)pyridin-3-yl ]pyridazine

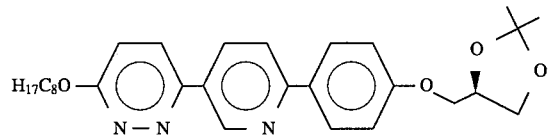

By etherification by the method of Mitsunobu (for example O. Mitsunobu, Synthesis 1981, 1) of 4-[5-(6-octyloxypyridazin-3-yl)pyridin-2-yl]phenol using S-(+)-2,2-dimethyl-4-hydroxymethyl-1,3-dioxolane.

EXAMPLE 6ai

3-Octyloxy-6-[6-(4-{(4R)-2,2-dimethyl[1,3 ]-dioxolane-4-carbonyloxy}phenyl)pyridin-3-yl ]pyridazine

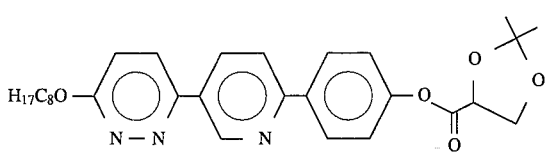

By esterification of 4-[5-(6-octyloxypyridazin-3-yl)pyridin-2-yl]phenol with R-(+)-2,2-dimethyl-1,3-dioxolane-4-carboxylic acid using dicyclohexylcarbodiimide (DCC) (for example A. Hassner, V. Alexanian, Tetrahedron Lett., (1978) 4475).

EXAMPLE 6aj

3-Octyloxy-6-[6-(4-{(2R,3R)-3-propyloxirane-2-carbonyloxy }phenyl)pyridin-3-yl]pyridazine

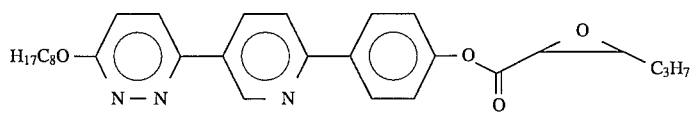

By esterification of 4-[5-(6-octyloxypyridazin-3-yl)pyridin-2-yl]phenol with (2R, 3R)-3-propyloxirane-2-carboxylic acid using DCC (for example A. Hassner, V. Alexanian, Tetrahedron Lett., (1978) 4475).

EXAMPLE 6ak

2-[6-(4-Benzyloxyphenyl)pyridin-3-yl]-5-octyloxypyrazine

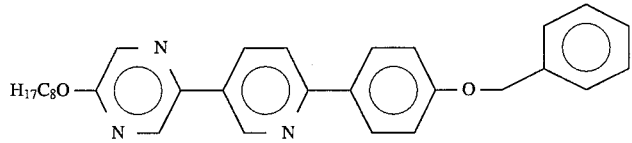

Step 1

In accordance with scheme C-I, 10 g of 2,5-dibromopyridine and 19.24 g of 4-benzyloxyphenylboronic acid are coupled analogously to Example 4a to give 21.2 g (73.9%) of 5-bromo-2-(4-benzyloxyphenyl)pyridine.

Step 2

In accordance with scheme C-III, 20 g (29.4 mmol ) of 5-bromo-2-(4-benzyloxyphenyl)pyridine are converted analogously to Example 3a into 2-(4-benzyloxyphenyl)pyridine-5-boronic acid.

Step 3

In accordance with scheme D, 2-(4-benzyloxyphenyl)pyridine-5-boronic acid is reacted with 2-chloro-5-octyloxypyrazine analogously to Example 4a to give 2-[6-( 4-benzyloxyphenyl)pyridin-3-yl ]-5-octyloxypyrazine.

EXAMPLE 6al

4-[5-(5-Octyloxypyrazin-2-yl)pyridin-2-yl]phenol

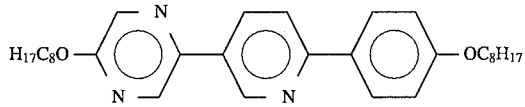

6.02 g (12.9 mmol) of 2-[6-(4-benzyloxyphenyl)pyridin-3-yl]-5-octyloxypyrazine are dissolved in 700 ml of absolute THF at 50° C., 3.0 g of palladium on charcoal are added, and the mixture is hydrogenated at 50° C. After filtration, the filtrate is evaporated in a rotary evaporator. The residue is chromatographed on $SiO_2$ using $CH_2Cl_2$/ethyl acetate, giving 4-[5-(5-octyloxypyrazin-2-yl)pyridin-2-yl]phenol.

EXAMPLE 6am

2-Octyloxy-5-[6-(4-octyloxyphenyl)pyridin-3-yl]pyrazine 0.6 g (1.6 mmol) of 4-[5-(5-octyloxypyrazin-2-yl)pyridin-2-yl]phenol is dissolved in 20 ml of DMF, 0.1 g of NaH (60% in mineral oil) is added at room temperature, the mixture is stirred for 30 minutes, and 0.46 g (2.4 mmol) of 1-bromooctane is then added. The mixture is stirred for a further 20 hours and poured into 200 ml of $H_2O$, and the precipitate is filtered off with suction. Purification is carried out by chromatography on $SiO_2$ using $CH_2Cl_2$/ethyl acetate: 95/5, giving 2-octyloxy-5-[6-(4-octyloxyphenyl)pyridin-3-yl]pyrazine.

EXAMPLE 6an

2-Octyloxy-5-[6-(4-{6-cyclopropylhexoxy}phenyl)pyridin-3-yl ]pyrazine

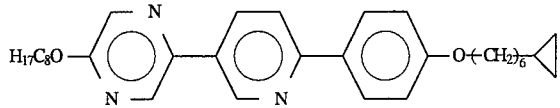

Analogously to Example 6ac from 4-[5-(5-octyloxy-pyrazin-2-yl)pyridin-2-yl]phenol and 6-cyclopropylhexyl bromide.

EXAMPLE 6ao

2-Octyloxy-5-[6-(4-{5-oxanonyloxy}phenyl)pyridin-3-yl ]pyrazine

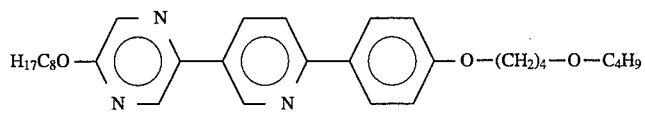

Analogously to Example 6ac from 4-[5-(5-octyloxy-pyrazin-2-yl)pyridin-2-yl]phenol and 5-oxanonyl bromide.

EXAMPLE 6ap

2-Octyloxy-5-[6-(4-{5-(dimethylsila)nonyloxy}phenyl)pyridin-3-yl ]pyrazine

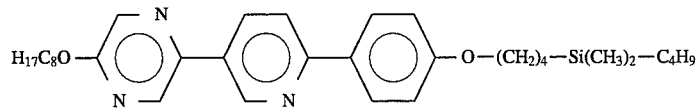

Analogously to Example 6ac from 4-[5-(5-octyloxy-pyrazin-2-yl)pyridin-2-yl]phenol and 5-(dimethylsila)nonyl bromide.

EXAMPLE 6aq

2-Octyloxy-5-[6-(4-{(2S,3S)-3-butyloxiran-2-ylmethoxy}phenyl)pyridin-3-yl]pyrazine

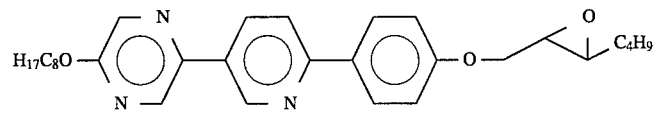

By etherification by the method of Mitsunobu (for example O. Mitsunobu, Synthesis 1981, 1) of 4-[5-(5-octyloxy-pyrazin-2-yl)pyridin-2-yl]phenol using (2S, 3S )-2-hydroxymethyl-3-butyloxirane.

EXAMPLE 6ar

2-Octyloxy-5-[6-(4-{(4S)-2,2-dimethyl[1,3 ]-dioxolan-4-ylmethoxy}phenyl)pyridin-3-yl]pyrazine

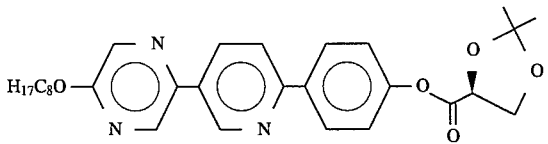

By etherification by the method of Mitsunobu (for example O. Mitsunobu, Synthesis 1981, 1) of 4-[5-(5-octyloxypyrazin-2-yl)pyridin-2-yl]phenol using S-( +)-2,2-dimethyl-4-hydroxymethyl-1,3-dioxolane.

EXAMPLE 6as

2-Octyloxy-5-[6-(4-{(4R)-2,2-dimethyl[1,3 ]-dioxolane-4-carbonyloxy}phenyl)pyridin-3-yl]pyrazine By esterification of 4-[5-(5-octyloxypyrazin-2-yl)pyridin-2-yl]phenol with R-(+)-2,2-dimethyl-1,3-dioxolane-4-carboxylic acid using DCC ( for example A. Hassner, V. Alexanian, Tetrahedron Lett., (1978) 4475).

EXAMPLE 6at

2-Octyloxy-5-[6-(4-{(2R,3R)-3-propyloxirane-2-carbonyloxy }phenyl)pyridin-3-yl]pyrazine

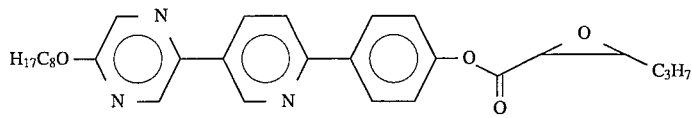

By esterification of 4-[5-(5-octyloxypyrazin-2-yl)pyrdin-2-yl]phenol with (2R,3R)-3-propyloxirane-2-carboxylic acid using DCC (for example A. Hassner, V. Alexanian, Tetrahedron Lett., (1978) 4475).

EXAMPLE 6ba 3-(4-Benzyloxyphenyl)-6-(6-octyloxypyridin-3-yl)pyridazine

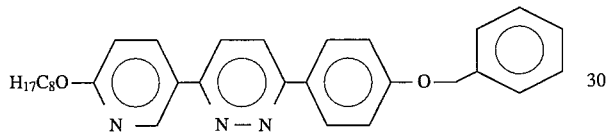

Step 1

In accordance with scheme C-I, 30 g (201 mmol) of 3,6-dichloropyridazine and 45.92 g (201 mmol) of 4-benzyloxyphenylboronic acid are coupled analogously to EXAMPLE 4a to give 14.5 g (24%) of 6-chloro-3-(4-benzyloxyphenyl)pyridazine.

(Melting point 187° C.)
Step 2

In accordance with scheme D, 14 g (47.2 mmol) of 6-chloro-3-(4-benzyloxyphenyl)pyridazine are reacted analogously to Example 4a with 11.8 g (47.2 mmol) of 2-octyloxypyridine-5-boronic acid to give 15.3 g of 3-(4-benzyloxyphenyl)-6-(6-octyloxypyridin-3-yl)pyridazine.

EXAMPLE 6bb

4-[6-(6-Octyloxypyridin-3-yl)pyridazin-3-yl]phenol

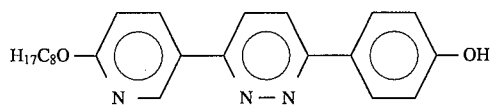

4.58 g (9.8 mmol ) of 3-(4-benzyloxyphenyl)-6-(6-octyloxypyridin-3-yl)pyridazine are dissolved in 100 ml of absolute THF at 50° C., 1.0 g of palladium on charcoal is added, and the mixture is hydrogenated at 50° C. After filtration, the filtrate is evaporated in a rotary evaporator. The residue is chromatographed on $SiO_2$ using $CH_2Cl_2$/ethyl acetate, giving 1.72 g of 4-[6-(6-octyloxpyridin-3-yl)pyridazin-3-yl]phenol.

EXAMPLE 6bc 3-(4-Octyloxyphenyl)-6-(6-octyloxypyridin-3-yl)pyridazine

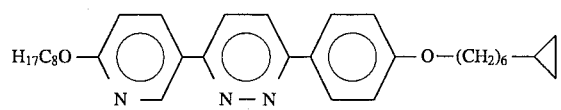

0.6 g (1.6 mmol) of 4-[6-(6-octyloxypyridin-3-yl)pyridazin-3-yl]phenol is dissolved in 20 ml of DMF, 0.1 g of NaH (60% in mineral oil) is added at room temperature, the mixture is stirred for 30 minutes, and 0.46 g (2.4 mmol) of 1-bromooctane is then added. The mixture is stirred for a further 20 hours and poured into 200 ml of $H_2O$, and the precipitate is filtered off with suction. Purification is carried out by chromatography on $SiO_2$ using $CH_2Cl_2$/ethyl acetate: 95/5, giving 0.43 g of 3-(4-octyloxyphenyl)-6-(6-octyloxypyridin-3-yl)pyridazine.

Phases X 109 $S_X$ 138 $S_C$ 233 I

EXAMPLE 6bd 3-(4-{6-Cyclopropylhexoxy}phenyl)-6-(6-octyloxypyridin-3-yl)pyridazine Analogously to Example 6bc from 4-[6-(6-octyloxypyridin-3-yl)pyridazin-3-yl]phenol and 6-cyclopropylhexyl bromide.

EXAMPLE 6be 3-(4-{5-Oxanonyloxy}phenyl)-6-(6-octyloxypyridin-3-yl)pyridazine

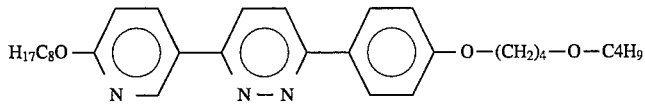

Analogously to Example 6bc from 4-[6-(6-octyloxypyridin-3-yl)pyridazin-3-yl]phenol and 5-oxanonyl bromide.

EXAMPLE 6bf 3-(4-{5-(Dimethylsila)nonyloxy}phenyl)-6-(6-octyloxypyridin-3-yl)pyridazine

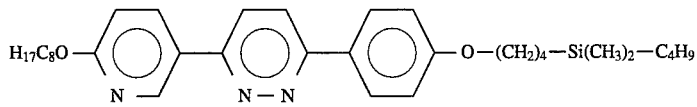

Analogously to Example 6bc from 4-[6-(6-octyloxypyridin-3-yl)pyridazin-3-yl]phenol and 5-(dimethylsila)nonyl bromide.

EXAMPLE 6bg 3-(4-{(2S, 3S )-3-Butyloxiran-2-ylmethoxy}phenyl)-6-(6-octyloxypyridin-3-yl)pyridazine

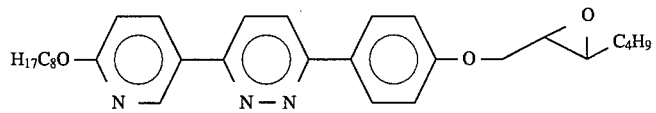

By etherification by the method of Mitsunobu (for example O. Mitsunobu, Synthesis 1981, 1) of 4-[6-(6-octyloxypyridin-3-yl)pyridazin-3-yl]phenol using (2S,3S)-2-hydroxymethyl-3-butyloxirane.

EXAMPLE 6bh 3-(4-{(4S)-2,2-Dimethyl-[1,3]-dioxolan-4-ylmethoxy}phenyl)-6-(6-octyloxypyridin-3-yl)pyridazine

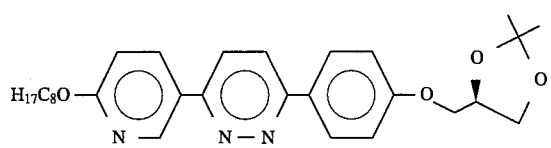

By etherification by the method of Mitsunobu (for example O. Mitsunobu, Synthesis 1981, 1) of 4-[6-(6-octyloxypyridin-3-yl)pyridazin-3-yl]phenol using S-(+)-2,2-dimethyl-4-hydroxymethyl-1,3-dioxolane.

EXAMPLE 6bi 3-(4-{(4R)-2,2-Dimethyl-[1,3 ]-dioxolane-4-carbonyloxy}phenyl)-6-(6-octyloxypyridin-3-yl)]pyridazine

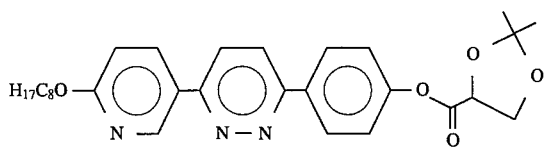

By esterification of 4-[6-(6-octyloxypyridin-3-yl)pyridazin-3-yl]phenol with R-(+)-2,2-dimethyl-1,3-dioxolane-4-carboxylic acid using DCC ( for example A. Hassner, V. Alexanian, Tetrahedron Lett., (1978) 4475).

Phases X 190 $S_C^*$ 218 $S_A$ 248 I

EXAMPLE 6bj 3-(4-{(2R,3R )-3-Propyloxirane-2-carbonyloxy}phenyl)-6-(6-octyloxypyridin-3-yl)pyridazine

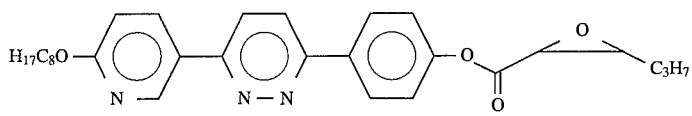

By esterification of 4-[6-(6-octyloxypyridin-3-yl)pyridazin-3-yl]phenol with (2R,3R)-3-propyloxirane-2-carboxylic acid using DCC (for example A. Hassner, V. Alexanian, Tetrahedron Lett. (1978) 4475).

Phases X 175 $S_A$ 169–172 I

EXAMPLE 6bk 2-(4-Benzyloxyphenyl)-5-(6-octyloxypyridin-3-yl)pyrazine

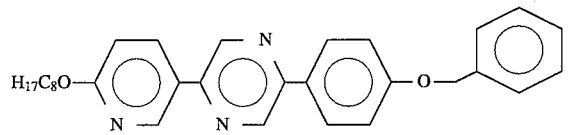

Step 1

In accordance with scheme C-I, 30 g (201 mmol) of 2,5-dichloropyrazine and 45.92 g (201 mmol) of 4-benzyloxyphenylboronic acid are coupled analogously to Example 4a to give 2-chloro-5-(4-benzyloxyphenyl)pyrazine.

Step 2

In accordance with scheme D, 14 g (47.2 mmol) of 2-chloro-5-(4-benzyloxyphenyl)pyrazine are reacted analogously to Example 4a with 11.8 g (47.2 mmol) of 2-octyloxypyridine-5-boronic acid to give 2-(4-benzyloxyphenyl)-5-(6-octyloxypyridin-3-yl)pyrazine.

EXAMPLE 6bl

4-[5-(6-Octyloxypyridin-3-yl)pyrazin-2-yl]phenol

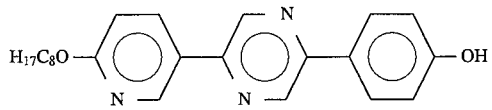

4.58 g (9.8 mmol) of 2-(4-benzyloxyphenyl)-5-(6-octyloxypyridin-3-yl)pyrazine are dissolved in 100 ml of absolute THF at 50° C., 1.0 g of palladium charcoal is added, and the mixture is hydrogenated at 50° C. After filtration, the filtrate is evaporated in a rotary evaporator. The residue is chromatographed on $SiO_2$ using $CH_2Cl_2$/ethyl acetate, giving 1.72 g of 4-[5-(6-octyloxypyridin-3-yl)pyrazin-2-yl]phenol.

EXAMPLE 6bm 2-(4-Octyloxyphenyl)-5-(6-octyloxypyridin-3-yl)pyrazine

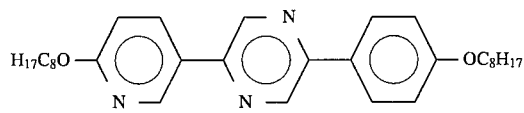

0.6 g (1.6 mmol) of 4-[5-(6-octyloxypyridin-3-yl)pyrazin-2-yl]phenol is dissolved in 20 ml of DMF, 0.1 g of NaH (60% in mineral oil) is added at room temperature, the mixture is stirred for 30 minutes, and 0.46 g (2.4 mmol) of 1-bromooctane is then added. The mixture is stirred for a further 20 hours and poured into 200 ml of $H_2O$, and the precipitate is filtered off with suction. Purification is carried out by chromatography on $SiO_2$ using $CH_2Cl_2$/ethyl acetate: 95/5, giving 2-(4-octyloxyphenyl)-5-(6-octyloxypyridin-3-yl)pyrazine.

EXAMPLE 6bn 2-(4-{6-Cyclopropylhexoxy}phenyl)-5-(6-octyloxypyridin-3-yl)pyrazine

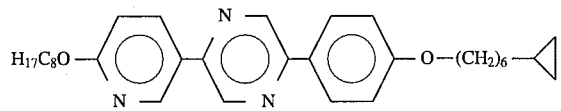

Analogously to Example 6bc from 4-[5-(6-octyloxypyridin-3-yl)pyrazin-2-yl]phenol and 6-cyclopropylhexyl bromide.

EXAMPLE 6bo 2-(4-{5-Oxanonyloxy}phenyl)-5-(6-octyloxypyridin-3-yl)pyrazine

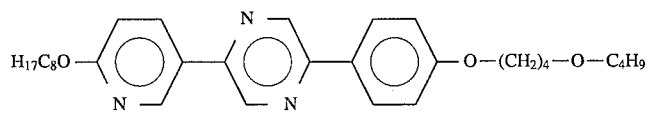

Analogously to Example 6bc from 4-[5-(6-octyloxypyridin-3-yl)pyrazin-2-yl]phenol and 5-oxanonyl bromide.

EXAMPLE 6bp 2-(4-{5-(Dimethylsila)nonyloxy}phenyl)-5-(6-octyloxypyridin-3-yl)pyrazine

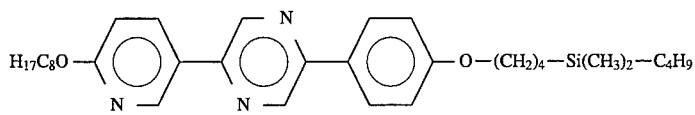

Analogously to Example 6bc from 4-[5-(6-octyloxypyridin-3-yl)pyrazin-2-yl]phenol and 5-( dimethylsila)nonyl bromide.

EXAMPLE 6bq 2-(4-{(2S,3S )-3-Butyloxiran-2-ylmethoxy}phenyl)-5-(6-octyloxypyridin-3-yl)pyrazine

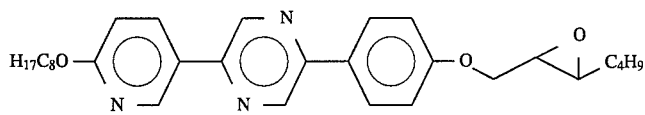

By etherification by the method of Mitsunobu (for example O. Mitsunobu, Synthesis 1981, 1) of 4-[5-(6-octyloxypyridin-3-yl)pyrazin-2-yl]phenol using (2S,3S )-2-hydroxymethyl-3-butyloxirane.

EXAMPLE 6br 2-(4-{(4S )-2,2-Dimethyl-[1,3]-dioxolan-4-ylmethoxy}phenyl)-5-(6-octyloxypyridin-3-yl)pyrazine

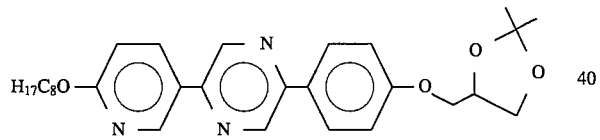

By etherification by the method of Mitsunobu (for example O. Mitsunobu, Synthesis 1981, 1) of 4-[5-(6-octyloxypyridin-3-yl)pyrazin-2-yl)pyrazin-2-yl]phenol using S-(+)-2,2-dimethyl-4-hydroxymethyl-1,3-dioxolane.

EXAMPLE 6bs 2-(4-{(4R )-2,2-Dimethyl-[1,3]-dioxolane-4-carbonyloxy}phenyl)-5-(6-octyloxypyridin-3-yl)]pyrazine

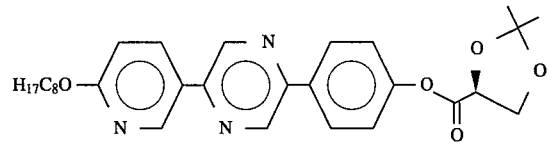

By esterification of 4-[5-(6-octyloxypyridin-3-yl)pyrazin-2-yl]phenol with R-(+)-2,2-dimethyl-1,3-dioxolane-4-carboxylic acid using DCC (for example A. Hassner, V. Alexanian, Tetrahedron Lett., (1978) 4475).

EXAMPLE 6bt 2-(4-{(2R,3R )-3-Propyloxirane-2-carbonyloxy}phenyl)-5-(6-octyloxypyridin-3-yl)pyrazine

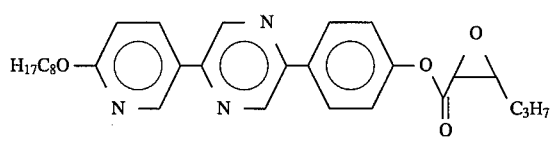

By esterification of 4-[5-(6-octyloxypyridin-3-yl)pyrazin-2-yl]phenol with (2R,3R)-3-propyloxirane-2-carboxylic acid using DCC (for example A. Hassner, V. Alexanian, Tetrahedron Lett., (1978) 4475).

Use Examples

Example A1

An achiral, ferroelectric liquid-crystal mixture A:

| | mol % |
|---|---|
| $C_8H_{17}$—⟨pyrazine⟩—⟨phenyl⟩—O—$C_6H_{13}$ | 21.45 |
| $C_8H_{17}$—⟨pyrazine⟩—⟨phenyl⟩—O—$C_8H_{17}$ | 14.30 |
| $C_8H_{17}$—O—⟨pyridine⟩—⟨phenyl⟩—O—$C_6H_{13}$ | 19.25 |
| $C_8H_{17}$—⟨pyrazine⟩—⟨phenyl⟩—O—$C_{10}H_{21}$ | 13.41 |

-continued

| | mol % |
|---|---|
| $C_8H_{17}-O-\underset{N}{\underset{\|}{\overset{N}{\overset{\|}{\bigcirc}}}}-\bigcirc-O-C_8H_{17}$ | 6.19 |
| $C_8H_{17}-O-\underset{N}{\underset{\|}{\overset{N}{\overset{\|}{\bigcirc}}}}-\bigcirc-O-C_4H_9$ | 14.14 |
| $C_8H_{17}-O-\underset{N}{\underset{\|}{\overset{N}{\overset{\|}{\bigcirc}}}}-\bigcirc-O-C_{10}H_{21}$ | 11.25 | exhibits the following liquid-crystalline phase ranges:

$S_C$ 63.5 $S_A$ 76.8 N 81.5 I

Addition of 10 mol % of 3-octyloxy-6-(6-hexoxypyridin-3-yl)pyridazine (Example 4c) to the mixture A results in a mixture having the following phase ranges:

$S_C$ 67 $S_A$ 76 N 80 I

Example A2

An achiral, ferroelectric liquid-crystal mixture B:

| | % by weight |
|---|---|
| $C_6H_{13}-O-\underset{N}{\underset{\|}{\overset{N}{\overset{\|}{\bigcirc}}}}-\bigcirc-O-C_6H_{13}$ | 3.48 |
| $\bigcirc\text{H}-\bigcirc-CO-O-\underset{N}{\underset{\|}{\overset{N}{\overset{\|}{\bigcirc}}}}-\bigcirc-O-C_8H_{17}$ | 12.69 |
| $C_7H_{15}-O-\underset{N}{\underset{\|}{\overset{N}{\overset{\|}{\bigcirc}}}}-\bigcirc-O-C_9H_{19}$ | 6.40 |
| $C_6H_{13}-O-\underset{N}{\underset{\|}{\overset{N}{\overset{\|}{\bigcirc}}}}-\bigcirc-O-C_8H_{17}$ | 6.58 |
| $C_8H_{17}-O-\underset{N}{\underset{\|}{\overset{N}{\overset{\|}{\bigcirc}}}}-\bigcirc-O-C_6H_{13}$ | 7.24 |
| $C_8H_{17}-O-\underset{N}{\underset{\|}{\overset{N}{\overset{\|}{\bigcirc}}}}-\bigcirc-O-C_8H_{17}$ | 7.77 |
| $C_6H_{13}-O-\bigcirc-CO-O-\underset{CH_3}{\bigcirc}-O-CO-\bigcirc-O-C_6H_{13}$ | 3.00 |
| $C_8H_{17}-O-\bigcirc-\bigcirc-O-CO-\bigcirc-O-C_4H_8-\underset{CH_3}{\overset{CH_3}{\underset{\|}{Si}}}-C_4H_9$ | 5.76 |
| $C_8H_{17}-O-\underset{N}{\overset{N}{\bigcirc}}-\underset{N}{\overset{N}{\bigcirc}}-O-C_8H_{17}$ | 3.98 |

| Structure | % by weight |
|---|---|
| C₁₀H₂₁—O—⟨phenyl⟩—CO—O—⟨phenyl⟩—O—C₄H₈—Si(CH₃)₂—C₄H₉ | 5.29 |
| C₁₀H₂₁—O—⟨phenyl⟩—⟨thiadiazole (N—N, S)⟩—⟨phenyl⟩ | 6.64 |
| C₁₀H₂₁—O—⟨phenyl⟩—CO₂—⟨phenyl⟩—O—C₃H₆—CH(CH₃)(C₂H₅) | 9.01 |
| C₃H₇—O—⟨phenyl⟩—⟨pyrimidine (N,N)⟩—⟨phenyl⟩—O—C₈H₁₇ | 6.30 |
| C₈H₁₇—O—⟨phenyl⟩—⟨fluoropyridine (N, F)⟩—⟨phenyl⟩—O—C₄H₈—Si(CH₃)₂—C₄H₉ | 8.12 |
| C₉H₁₉—CO—O—⟨pyridazine (N,N)⟩—⟨phenyl⟩—O—C₈H₁₇ | 7.73 | exhibits the following liquid-crystalline phase ranges:

$S_C$ 79.5 $S_A$ 90.5N 102 I

Addition of 10% by weight of 3-octyloxy-6-[6-(4-octyloxyphenyl)pyridin-3-yl]pyridazine (Example 6ac) to the mixture B results in a mixture having the following phase ranges:

$S_C$ 93 $S_A$ 99N 114 I

EXAMPLE A3

Addition of 10% by weight of 3-octyloxy-6-[6-(4-{(2S, 3S)-3-butyloxiran-2-ylmethoxy}phenyl)pyridin-3-yl]pyridazine (Example 6ag) to the mixture B results in a novel mixture having the following phase ranges:

$S_C$ 94 $S_A$ 101N 114 I
The mixture has a $P_s$ value of +7 nC/cm² at 20° C.

Example A4

Addition of 10% by weight of 3-octyloxy-6-(6-octyloxypyridin-3-yl)pyridazine (Example 4a) to the mixture B results in a novel mixture having the following phase ranges:

$S_C$ 80 $S_A$ 89N 98 I

Example A5

Addition of 10% by weight of 3-(4-{(2R,3R)-3-propyloxirane-2-carbonyloxy}phenyl)-6-(6-octyloxypyridin-3-yl)pyridazine (Example 6bj) to the mixture B results in a novel mixture having the following phase ranges:

$S_C$ 88 $S_A$ 95N 104 I

A mixture containing 5% by weight of the compound according to the invention has a $P_s$ value of +22.8 nC/cm² at 40° C.

EXAMPLE A6

Addition of 10% by weight of 3-(4-{(4R)-2,2-dimethyl [1,3]-dioxolane-4-carbonyloxy}phenyl)-6-(6-octyloxypyridin-3-yl)pyridazine (Example 6bi) to the mixture B results in a novel mixture having the following phase ranges:

$S_C$ 92 $S_A$ 98.5N 111 I

The strong tendency of the compounds according to the invention to raise the phase transitions is evident.

Comparative Example V1

The compound 2-(4-{(2R,3R)-3-propyloxirane-2-carbonyloxy}phenyl)-5-(6-octyloxypyridin-3-yl)pyrimidine, which has already been disclosed, has the following phase ranges:

X 77 $X_1$ 120 $S_2$ 119 $S_A$ 136 I

Addition of 10% by weight of 2-(4-{(2R,3R)-3-propyloxirane-2-carbonyloxy}phenyl)-5-(6-octyloxypyridin-3-yl)pyrimidine to the mixture B results in a novel mixture having the following phase ranges:

$S_C$ 81 $S_A$ 96N 102 I

A mixture containing 5% by weight of the compound according to the invention has a $P_s$ value of +19.4 nC/cm² at 40° C.

Compared with Example A5, it can be seen that there is virtually no tendency to broaden the $S_C$ phase range, rather a strong tendency to broaden the $S_A$ phase range. The induced $P_s$ value is likewise lower than achieved by the structurally similar compound according to the invention in A5.

We claim:

1. A ferroelectric liquid-crystalline mixture comprising at least one compound of the formula (I)

in which the symbols and indices have the following meanings:

—U— is selected from the group consisting of

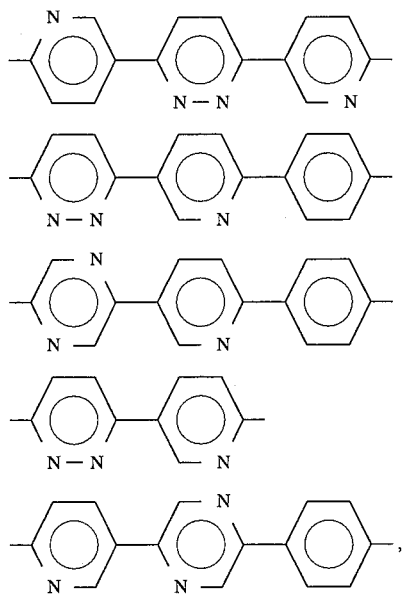

and

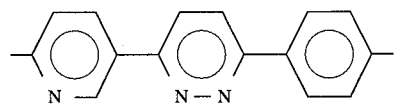

$R^1$ and $R^2$ are, independently of one another, a straight-chain or branched alkyl radical having 1 to 20 carbon atoms (with or without asymmetrical carbon atoms), it also being possible for one or more $CH_2$ groups to be replaced by —O—, —CO—,

—Si(CH$_3$)$_2$—, or 1,4-phenylene, with the proviso that oxygen atoms must not be bonded directly to one another, or one of the following chiral groups:

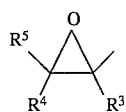

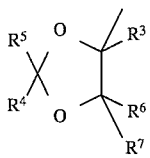

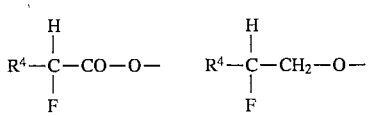

$R^3$, $R^4$, $R^5$, $R^6$ and $R^7$ are, independently of one another, hydrogen or a straight-chain or branched alkyl radical having 1–16 carbon atoms (with or without asymmetrical carbon atoms), it also being possible for one or more $CH_2$ groups to be replaced by —O—, with the proviso that oxygen atoms must not be bonded directly to one another, $R^4$ and $R^5$ together may also be —(CH$_2$)$_4$— or —(CH$_2$)$_5$— if they are bonded to an oxirane or dioxolane;

$M^1$ and $M^2$ are, independently of one another, —O—, —CO—O—, —O—CO—, —CH$_2$—O— or —O—CH$_2$—;

a and d are zero; and b and c are zero or one;

m and n are zero or one.

2. An azaaromatic compound of the general formula I

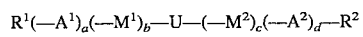

in which the symbols and indices have the following meanings:

—U— is selected from the group consisting of:

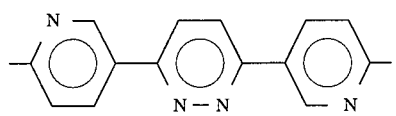

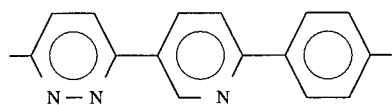

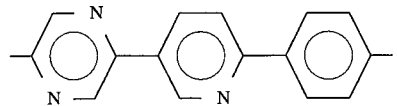

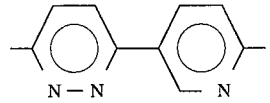

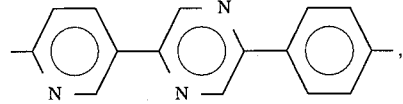

and

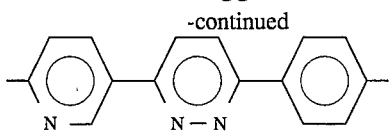

$R^1$ and $R^2$ are, independently of one another, a straight-chain or branched alkyl radical having 1 to 20 carbon atoms (with or without asymmetrical carbon atoms), it also being possible for one or more $CH_2$ groups to be replaced by —O—, —CO—,

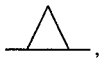

—Si(CH$_3$)$_2$— or 1,4-phenylene, with the proviso that oxygen atoms must not be bonded directly to one another, or one of the following chiral groups:

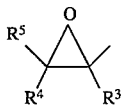

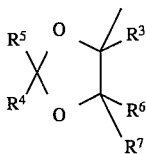

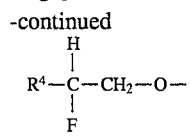

$R^3$, $R^4$, $R^5$, $R^6$ and $R^7$ are, independently of one another, hydrogen or a straight-chain or branched alkyl radical having 1–16 carbon atoms (with or without asymmetrical carbon atoms), it also being possible for one or more $CH_2$ groups to be replaced by —O—, with the proviso that oxygen atoms must not be bonded directly to one another, $R^4$ and $R^5$ together may also be —(CH$_2$)$_4$— or —(CH$_2$)$_5$— if they are bonded to an oxirane or dioxolane;

$M^1$ and $M^2$ are, independently of one another, —O—, —CO—O—, —O—CO—, —CH$_2$—O— or —O—CH$_2$—;

a and d are zero; and b and c are zero or one.

3. The ferroelectric liquid-crystalline mixture as claimed in claim 1, which consists of 2 to 20 components.

4. The ferroelectric liquid-crystalline mixture as claimed in claim 1, which comprises from 0.01 to 80% by weight of one or more compounds of the formula I.

5. An electro-optical switching and/or display element comprising a liquid-crystalline mixture as claimed in claim 1.

* * * * *